US006969516B1

(12) United States Patent
Steeves et al.

(10) Patent No.: US 6,969,516 B1
(45) Date of Patent: Nov. 29, 2005

(54) IMMUNOLOGICAL COMPOSITIONS AND METHODS OF USE TO TRANSIENTLY ALTER MAMMALIAN CENTRAL NERVOUS SYSTEM MYELIN TO PROMOTE NEURONAL REGENERATION

(75) Inventors: John D. Steeves, North Vancouver (CA); Jason K. Dyer, North Vancouver (CA); Hans S. Keirstead, Irvine, CA (US)

(73) Assignee: MBM & Co., Ottawa (CA)

( * ) Notice: Subject to any disclaimer, the term of this patent is extended or adjusted under 35 U.S.C. 154(b) by 0 days.

(21) Appl. No.: 09/530,234

(22) PCT Filed: Oct. 28, 1998

(86) PCT No.: PCT/CA98/00997

§ 371 (c)(1),
(2), (4) Date: Jul. 6, 2000

(87) PCT Pub. No.: WO99/21581

PCT Pub. Date: May 6, 1999

(30) Foreign Application Priority Data

Oct. 28, 1997 (CA) .................................. 2219683
Oct. 16, 1998 (CA) .................................. 2251410

(51) Int. Cl.[7] ..................... A61K 39/395; A61K 51/00; C12N 5/06; C07K 16/00
(52) U.S. Cl. ............... 424/130.1; 424/141.1; 424/172.1; 424/1.41; 530/387.1; 435/337
(58) Field of Search .............................. 514/2, 12, 21; 424/130.1, 152.1, 141.1, 172.1, 1.41; 530/387.1; 435/337; 436/821

(56) References Cited

OTHER PUBLICATIONS

Barinaga, M., 1994, Science, 264, pp. 772-774.*
Bregman et al., "Recovery from Spinal Cord Injury Mediated by Antibodies to Neurite Growth Inhibitors", *Nature*, 378:498-501 (1995).
Caroni et al., "Antibody Against Myelin-Associated Inhibitor of Neurite Growth Neutralizes Nonpermissive Substrate Properties of CNS White Matter," *Neuron*, 1: 85-96 (1988).
Dubois-Dalco et al., "Action of Anti-Cerebroside Sera on Myelinated Nervous Tissue Cultures", *Path. Europ.*, 5(3): 331-347 (1970).
Dyer et al., "Glycolipids and Transmembrane signaling: Antibodies to Galactocerebroside Cause an Influx of Calcium in Oligondendrocytes", *J. Cell Biol.*, 111:625-633 (1990).
Dyer et al., "Antibodies to Myelin/Oligodendrocyte-Specific Protein and Myelin/Oligodendrocyte Glycoprotein Signal Distinct Changes in the Organization of Cultured Oligondendroglial Membrane Sheets," *J. of Neurochemistry*, 62:777-787 (1994).
Keirstead et al., "Identification of post-mitotic oligodendrocytes incapable of remyelinatio within the demyelinated adult spinal cord," *Journal of Neuropathy & Experimental Neurology*, 56(11):1191-1201 (Nov. 1997).
Linington et al., "Induction of Persistently Demyelinated Lesions In the Rat Following the Repeated Adoptive Transfer of Encephalitogenic T Cells and Demyelinating Antibody," *J. Neuroimmunol*, 40(2-3):219-224 (1992).
Meeson, A.P. et al., "The Distribution of Inflammatory Demyelinated Lesions In the Central Nervous System of Rats With Antibody-Augmented Demyelinating Experimental Allergic Encephalomyelitis," *Exp. Neurol*, 129(2):299-310 (1994).
Keirstead et al., "In Vivo Immunological Suppression of Spinal Cord Myelin Development," *Brains Res. Bull.*, 44: 727-734 (1997).

* cited by examiner

Primary Examiner—Olgan N. Chernyshev
(74) Attorney, Agent, or Firm—DLA Piper Rudnick Gray Cary US LLP

(57) ABSTRACT

A method is described comprising the combined administration of a novel composition comprising serum complement proteins with complement-fixing antibodies to induce transient disruption of myelin and/or demyelination. The antibodies specifically bind to one or more epitopes of myelin, and complement proteins. A method is also described for promoting regrowth, repair, and regeneration of neurons in a mammalian subject. The methods can be used following immediate or chronic injury.

5 Claims, 10 Drawing Sheets

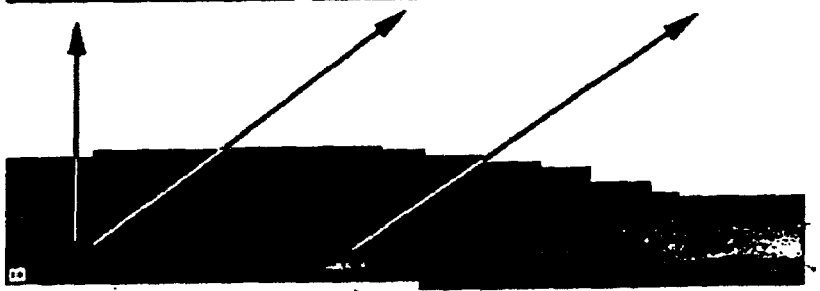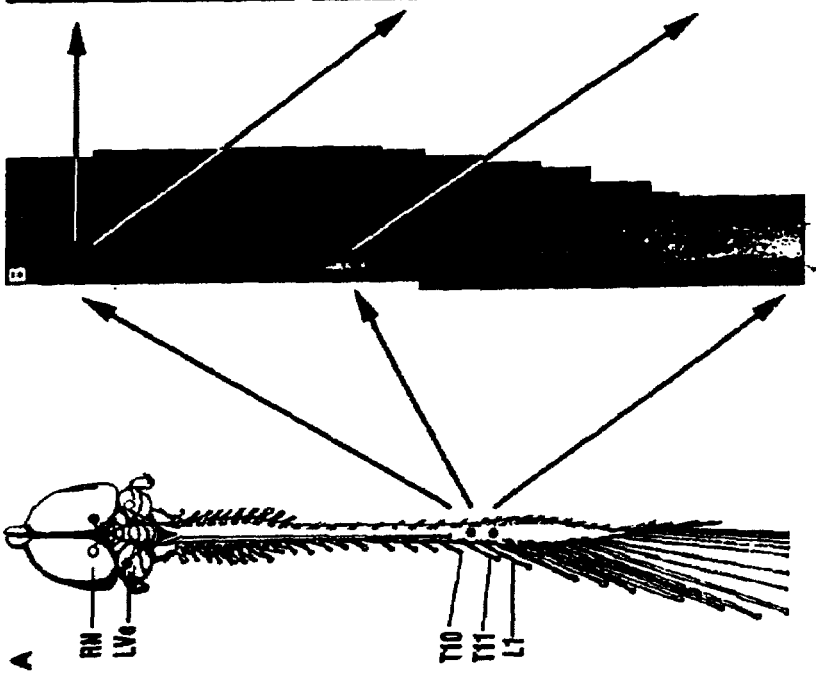

Figure 1A:
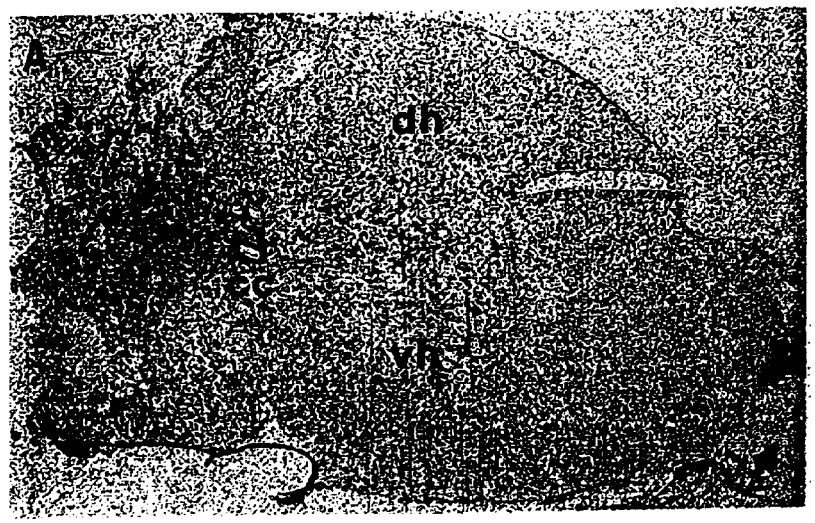

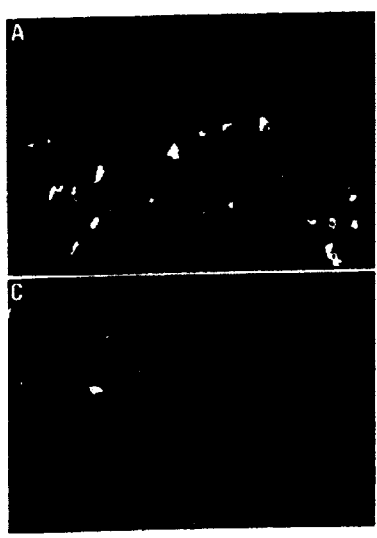
Figure 8A
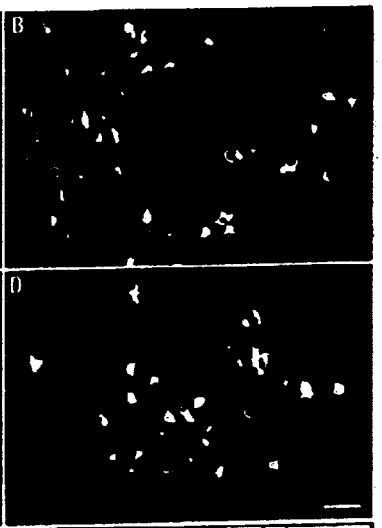
Figure 8B
Figure 8C
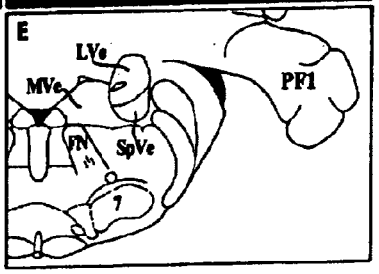
Figure 8D
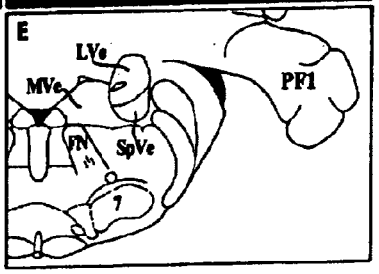
Figure 8E

IMMUNOLOGICAL COMPOSITIONS AND METHODS OF USE TO TRANSIENTLY ALTER MAMMALIAN CENTRAL NERVOUS SYSTEM MYELIN TO PROMOTE NEURONAL REGENERATION

FIELD OF THE INVENTION

This invention relates to compositions and their methods of use in promoting the growth and/or regeneration of neurological tissue within the central nervous system (CNS).

BACKGROUND

CNS damage

Approximately 1,100 new spinal cord injuries occur each year in Canada; over 10,000 per year occur in the United States. These numbers are five times higher if one also includes patients suffering brain damage involving inhibition to neural growth following traumatic brain injury. The number of patients with chronic spinal cord injuries in North America is in the order of 300,000. Again, this number is five times higher if one includes patients suffering from brain damage involving inhibition to neural growth following traumatic brain injury.

Spinal cord injuries often result in a permanent loss of voluntary movement below the site of damage. Mostly young and otherwise healthy persons become paraplegic or quadriplegic because of spinal cord injuries. There are an estimated 200,000 quadriplegics in the United States. Given the amount of care required, it is not difficult to envision how health care costs associated with caring for patients with central nervous system (CNS) damage is well over $10 billion a year for North America. The CNS (the brain and the spinal cord) is comprised of neurons and glia, such as astrocytes, microglia, and oligodendrocytes. Neurons typically have two types of processes: dendrites, which receive synaptic contact from the axons of other neurons: and axons, through which each neuron communicates with other neurons and effectors. The axon of a CNS neuron is wrapped in a myelin sheath.

In higher vertebrates, axons within the CNS possess a limited capacity for repair after injury. Axotomized neurons of the adult mammalian CNS fail to exhibit substantial axonal regeneration, in contrast to neurons within the embryonic or neonatal CNS or within the adult peripheral nervous system (PNS) (Saunders et al., (1992) *Proc. R. Soc. Lond. B. Biol.* 250: 171–180; Schwab and Bartoldi (1996) *Physiol. Rev.* 76:319–370; Steeves et al., (1994) *Prog. Brain Res.* 103: 243–262) In fact, complete CNS axonal disruption is likely to preclude recovery. Although axotomized fibers proximal to the neuronal cell body initiate regenerative growth, this is subsequently aborted within a short distance (1–2 mm) and is often followed by retrograde degeneration. Although CNS axons will not regrow in the environment of the adult spinal cord, peripheral nerve grafts into the CNS provide a favorable environment through which CNS axons will anatomically regenerate (May et al., *Cajal's Degeneration and Regeneration of the Nervous System, History of Neuroscience Series* #5(NY and Oxford: Oxford Univ. Press, 1991) at 769). These findings indicate that adult CNS neurons retain intrinsic growth properties and, given favorable environmental conditions, are capable of successfully reactivating growth programs.

Current Treatments of Spinal Cord Injuries

A number of current therapies exist for the treatment of spinal cord injuries. Interventional therapies, including opiate antagonists, thyrotropin-releasing hormone, local cord cooling, dextran infusion, adrenergic blockade, corticosteroids, and hyperbaric oxygen have been utilized, but are of questionable clinical value.

Peripheral nerve transplants have been suggested as bridges across CNS lesions (David and Aguayo (1981) *Science* 214:931–933, Houle (1991) *Exp. Neurol.* 113:1–9; Richardson et al., (1984)*J. Neurocytol.* 13:165–182; Richardson et al., (1980) *Nature* 284:264–265; Xu et al., (1995) *Exp. Neurol.* 138:261–276; Ye and Houle (1997) *Exp. Neurol.* 143:70–81). Olfactory ensheathing cell transplants have been used recently to promote there generation of injured corticospinal projections in the rat (Li et al., (1997) *Science* 277:2000–2002). A recent study (Cheng et al., (1996) *Science* 273:510–513) employed a combinatorial approach that extended earlierwork (Siegal et al., (1990) *Exp. Neurol.* 109:90–97): after transection of the adult rat spinal cord, peripheral grafts were used to connect white matter tracts to central gray matter in such a way as to direct regenerating fibers out of an inhibitory environment and into the more permissive gray matter.

U.S. Pat. Nos. 5,650,148 and 5762926 describe a method for treating damage to the CNS by grafting donor cells into the CNS that have been modified to produce molecules such as neurotrophins.

The use of transplanted neural cells is also of limited clinical value: although axons will be able to grow into the transplanted tissue, they will not be able to grow out of the transplanted tissue back into the CNS due to inhibitory matter in the CNS.

This review of current methods of treating spinal cord injuries indicates that a need remains for a means of promoting regrowth, repair, and regeneration of neurons in the mammalian CNS in both the acute and chronic situations.

Myelin

It has been suggested that the failure of CNS axons to regenerate after injury is associated with the presence of myelin. The myelin sheath wrapping an axon is composed of compacted plasma membranes of Schwann cells and oligodendrocytes. Although its composition resembles that of any other plasma membrane in that it contains lipids, proteins, and water, the relative proportions and dispositions of these components are unique to myelin. Myelin in the CNS is produced by oligodendrocytes and is characterized by the expression of myelin basic protein (MBP). MBP is only associated with myelin and is one of the first proteins expressed at the onset of myelination of CNS axonal fibers. Galactocerebroside (GalC) is the major sphingolipid produced by oligodendrocytes. GalC comprises approximately 15 percent of the total lipid in human myelin and is highly conserved across species. Although GalC is expressed on the surface of oliogodendrocyte cell bodies, it is expressed in greater concentration on the surface of myelin membranes (Ranscht et al., (1982) *Proc. Natl. Acad. Sci. USA* 79:2709–2713).

There is growing evidence that the presence of CNS myelin can retard or inhibit the regenerative growth of some severed CNS axons (Schwab and Bartoldi (1996) *Physiol. Rev.* 76:319–370), including a number of examples from widespread vertebrate families (Schwegler et al., (1995) *J. Neurosci.* 15:2756–2767. Steeves et al., (1994) *Prog. Brain Res.* 103:243–262). Both the lower vertebrate CNS (e.g. lamprey) and the developing CNS of higher vertebrates (e.g.

birds and mammals) exhibit substantial axonal regeneration after injury (Davis and McClellan (1994) *J. Comp. Neurol.* 344:65–82, Hasan et al., (1993) *J. Neurosci.* 13:492–507; Hasan et al., (1991) *Restor. Neurol. Neurosci.* 2:137–154; Iwashita et al., (1994) *Nature* 367: 167–170; Saunders et al., (1992) *Proc. R. Soc. Lond. B. Biol.* 250:171–180; Treherne et al., (1992) *Proc. Natl. Acad. Sci. USA* 89:431–434, Varga et al., (1995) *Eur. J. Neurosci.* 7:2119–2129). The common phenotype for all these positive examples of regeneration is either a CNS that lacks compact myelin (lamprey) or incomplete myelin development (embryonic chick, neonatal opossum and rat) at the time of injury. The developmental appearance of myelin temporally correlates with the loss of regeneration by injured CNS axons. In addition, the robust growth of transplanted fetal neurons in the adult CNS (Bregman et al., (1993) *Exp. Neurol.* 123:3–16; Li and Raisman (1993) *Brain Res.* 629:115–127, Yakovleff et al., (1995) *Exp. Brain Res.* 106:69–78) may be partially attributed to either a lack of receptors for myelin inhibitors at that stage of their differentiation and/or an ability to override any inhibitory signals from myelin.

Specific molecules associated with myelin have been identified as putative mediators of this inhibitory activity, including myelin-associated glycoprotein (MAG) (McKerracher et al., (1994) *Neuron.* 13:805–811; Mukhopadhyay et al., (1994) *Neuron.* 13:757–767) and NI35/250, an as yet unidentified myelin-derived protein (Bandtlow and Schwab (1991) *Soc. Neurosci. Abstr.* 17:1495; Caroni and Schwab (1988) *J. Cell Biol.* 106:1281–1288, Caroni and Schwab (1988) *Neuron* 1:85; Crutcher (1989) *Exp. Neurol.* 104: 39–54; Savio and Schwab (1989) *J. Neurosci.* 9:1126–1133; Schwab and Caroni (1988) *J. Neurosci.* 8:2381–2393); IN-1 (Brosamle, et al, (1998) *Abst. Soc Neurosci.,* 4:1559; NI-35/250 (Huber et al., (1998) *Abst. Soc Neurosci.,* 24:1559; NI-220/250 (van der Haar et al., (1998) *Abst. Soc Neurosci.,* 24: 1559; arretin, Janani et al., (1998) *Abst. Soc Neurosci.,* 24:1560; and NOGO (Chen et al., (1998) *Abst. Soc Neurosci.,* 24:1776.

Experimental attempts to functionally block myelin-associated inhibition involving NI35/250, by using an anti-NI35/250 antibody, IN-1, have facilitated some anatomical regeneration of corticospinal axons (Bregman et al., (1995) *Nature* 378:498–501; Caroni and Schwab (1988) *Neuron.* 1:85–96; Schnell and Schwab (1990) *Nature* 343:269–272).

The immunological disruption of mature myelin within the avian spinal cord (Keirstead et al., (1995) *J. Neurosci.* 15:6963–6974), and the delay of onset of CNS myelination during normal avian or mammalian neurodevelopment (Keirstead et al. (1992) *Proc. Natl. Acad. Sci. (USA)* 89:11664–11668; Keirstead et al., (1997) *Brain. Res. Bull.* 44:727–734, Varga et al., (1995) *Eur. J. Neurosci.* 7:2119–2129) have also facilitated CNS axonal re-growth and/or sprouting.

The presence of certain components located or embedded in myelin that are inhibitory to the regeneration of axonal growth after injury makes it desirable to transiently remove myelin and its inhibitory components to promote the repair of injured adult spinal cord. Adult spinal cord can be demyelinated in vivo via drugs (e.g. ethidium bromide), however, these drugs have non-specific deleterious effects on other cell types in the central nervous system (e.g., astrocytes). In addition, myelin-deficient strains of mice and rats are readily available, but are of limited experimental value due to a shortened life span: most do not survive beyond a couple of weeks after birth.

Consequently, there is a need for improved methods of disrupting myelin in vivo in order to enhance regeneration of neurological tissue. The present invention provides methods that address this need.

Complement

The complement system is the primary humoral mediator of antigen-antibody reactions. It consists of at least 20 chemical and immunologically distinct serum proteins capable of interacting with one another, with antibody, and with cell membranes (see, for example, J. Klein, *Immunology: The Science of Self-Nonself Discrimination* (New York: John Wiley & Sons, 1982) at 310–346). The principal actors in this system are 11 proteins, designated C1 to C9, B, and D, which are present normally among the plasma proteins. These proteins are normally inactive, but they can be activated in two separate ways: the classical pathway or the alternate pathway.

The classical pathway is activated by an antigen-antibody reaction: when an antibody binds with an antigen, a specific reactive site on the constant portion of the antibody becomes activated, which in turn binds directly with the C1 molecule of the complement system. This sets into motion a cascade of sequential reactions, beginning with the activation of the C1 proenzyme. Only a few antigen-antibody combinations are required to activate many molecules in this first stage of the complement system. The C1 enzymes then activate successively increasing quantities of enzymes in the later stages of the complement system. Multiple end-products are formed, which cause important effects that help to prevent damage by an invading organism or toxin, including opsonization and phagocytosis, lysis, agglutination, neutralization of viruses, chemotaxis, activation of mast cells and basophils, and inflammatory effects.

The complement system can also be activated by an alternate pathway without the intermediation of an antigen-antibody reaction. Certain substances react with complement factors B and D, forming an activation product that activates factor C3, setting off the remainder of the complement cascade; thus, essentially all the same final products of the system are formed as in the classical pathway, causing the same effects. Since the alternate pathway does not involve an antigen-antibody reaction, it is one of the first lines of defense against invading microorganisms.

Since components of both the classical pathway and the alternative pathway of the complement system act locally to activate C3, this is the pivotal component of complement. C3 is a 195 kD protein, which comprises two disulfide bridged chains of 105 and 75 kD. The enzymatically active C4-C2complex, activated in the classical pathway by the binding of C1 q to an antigen-antibody complex, cleaves C3 into two fragments, C3a and C3b. The larger fragment, C3b, binds covalently to the surface of a target cell where it acts as a protease to catalyze the subsequent steps in the complement cascade. It is also recognized by specific receptor proteins on macrophages and neutrophils that enhance the ability of these cells to phagocytose the target cell. In particular, membrane-immobilized C3b triggers a further cascade of reactions that leads to the assembly of membrane attack complexes from the late components.

Complement fixation by cell-surface binding antibodies has been shown to compromise the ionic homeostasis of many different cells in vitro within minutes of activation (Mayer (1972) *Proc. Natl. Acad. Sci. USA* 69:2954–2958; Morgan (1989) *Biochem. J.* 264:1–14).

Use of Complement with Myelin-Specific Antibodies

After attachment of a specific complement-fixing antibody to a myelin surface antigen, serum complement forms a membrane attack complex through an enzymatic cascade resulting in a rapid influx of extracellular calcium (Dyer and Benjamins (1990) *J. Cell Biol.* 111: 625–633) and subsequent cytoskeletal re-arrangement (Dyer and Matthieu (1994) *J. Neurochem.* 62:777–787). In vivo, this would make the disrupted myelin processes a target for phagocytosis by subsequent microglia, as well as by any invading macrophages.

The in vitro application of serum complement with myelin-specific antibodies has been shown to suppress myelin elaboration in purified oligodendrocyte cultures (Dorfman et al., (1979) *Brain Res.* 177:105–114, Dubios-Dalcq et al., (1970) *Pathol. Eur.* 5:331–347, Dyer and Benjamins (1990) *J. Cell Biol.* 111:625–633; Fry et al., (1974) *Science* 183:540–542; Hruby et al., (1977) *Science* 195:173–175).

In vivo myelin disruption has been shown in the guinea pig optic nerve using anti-GalC serum and complement (Sergott et al., (1984) *J Neurol. Sci.* 64:297–303); myelin disruption was observed within 1 to 2 hours of treatment.

The Chick Model

In the avian model, the onset of myelination in the embryonic chick spinal cord at E13 coincides with the transition from a permissive to a restrictive period for the functional repair of transected spinal cord. The first appearance of chick oligodendrocytes on the tenth and eleventh embryonic day of development (E10–E11) precedes the initial formation of myelin by 2–3 embryonic days and is characterized by the expression of galactocerebroside (GalC), the major sphingolipid produced by oligodendrocytes.

In the mature avian spinal cord, after spinal cord transection, immunological disruption of local spinal cord myelin facilitated regeneration by brainstem-spinal neurons (Keirstead et al., (1995) *J. Neurosci.* 15:6963–6974, Keirstead et al., (1997) Brain Res. Bull., 44:727–734). The immunological disruption of myelin was transient, produced by an intraspinal infusion of both serum complement and a myelin-specific, complement-fixing antibody (e.g. GalC antibodies). Such treatment resulted in the regeneration of up to 20% of mature brainstem-spinal axons.

This background information is provided for the purpose of making known information believed by the applicant to be of possible relevance to the present invention. No admission is necessarily intended, nor should be construed, that any of the preceding information constitutes prior art against the present invention. Publications referred to throughout the specification are hereby incorporated by reference in their entireties in this application.

SUMMARY OF THE INVENTION

The purpose of the present invention is to provide a means of promoting regrowth, repair, and regeneration of neurons in the mammalian CNS. Accordingly, the invention provides compositions and methods of use for promoting regrowth, repair, and/or regeneration of neurons in the CNS of a mammalian subject, such as a human, in both chronic and acute disorders.

One embodiment of the present invention provides a composition comprising therapeutically effective amounts of the following:

(a) one or more complement-fixing antibodies or fragments thereof, which specifically bind to an epitope of myelin; and (b) one or more complement proteins or fragments thereof, wherein the binding of said antibodies to myelin causes transient disruption and/or transient demyelination of myelin. The antibodies may be monoclonal and/or polyclonal. The complement proteins or fragments thereof may be derived from a species different from that species to which it is administered. In a preferred embodiment, the complement proteins or fragments thereof are human. The complement component may be a physically distinct component from the antibody component, or it may be covalently or noncovalently attached directly to the antibody component, such that binding of the antibody to the surface of the myelin triggers the endogenous immune system attack. One or more growth factors may be added (in an appropriate sequence) to facilitate regrowth and regeneration.

In a specific embodiment, the epitope of myelin is a myelin sheath epitope, such as galactocerebroside (GalC), 04, Myelin Oligodendrocyte Glycoprotein (MOG), or Myelin Associated Glycoprotein (MAG), NOGO, NI22, NI-35/250, or arretin, or fragments thereof. In a preferred embodiment, the epitope of myelin is GalC. Another preferred embodiment is MOG.

In a preferred embodiment, the complement proteins or fragments thereof include the C3 component or a fragment, variant, analog, or chemical derivative thereof. In a preferred embodiment, the component C3b is used.

In another embodiment of the present invention, the composition further comprises neurotrophins and growth factors, such as NT-3, CNTF, FGF-1, BDNF, PDGF, GDNF, CT-1, or BNP.

The present invention also relates to the use of these compositions to promote regrowth, repair, and/or regeneration of neurons in a subject by the transient disruption and/or transient demyelination of myelin.

In one embodiment of the present invention, the compositions are used in subjects requiring neuron repair and/or regeneration due to neuron dysfunction. This neuron dysfunction may be a result of acute or chronic injury to the CNS. It may also be a result of degenerative disease, such as Alzheimer's or Parkinson's disease.

In another embodiment of the present invention, the compositions are used in subjects to generate an environment within the CNS that is relatively permissive to growth of transplanted cells The present invention also relates to a method of promoting regrowth, repair, and regeneration of neurons in mammalian CNS, wherein the damage resulted from either a chronic or acute disorder. The method entails delivery of one or more complement-fixing antibodies or fragments thereof, which specifically bind to an epitope of myelin and delivery of one or more complement proteins or fragments thereof, delivered either together or separately to effect transient disruption and/or transient demyelination of myelin in the neuronal zone requiring regeneration.

Various other objects and advantages of the present invention will become apparent from the detailed description of the invention.

TABLES AND FIGURES

Table 1 presents rubrospinal neuronal cell counts obtained from individual control and experimental animals with retrograde Fluorogold labeling from the lumbar cord of an adult rat.

Figure 1B:
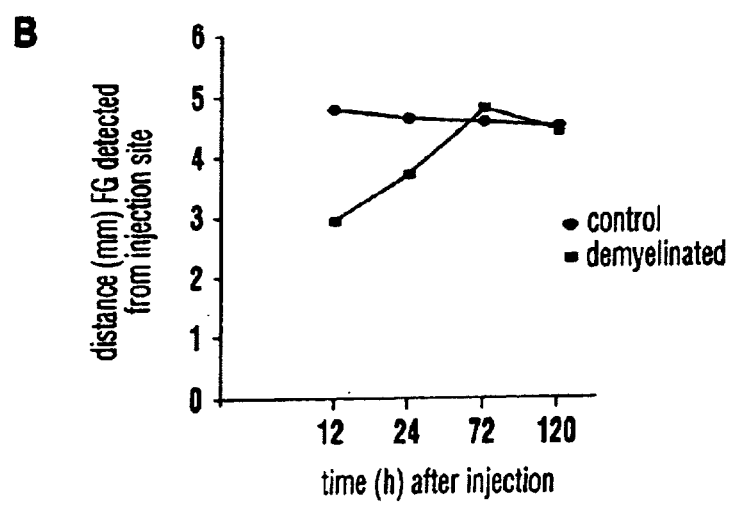

FIG. 1A presents Photomicrograph of a transverse section of spinal cord of an adult rat at the level of T10 left side hemisection lesion, stained with cresyl violet. All lesions were assessed and always resulted in severing the funiculi through which the rubrospinal tract traverses. The contralateral dorsal (dh) and ventral (vh) horns were always left undamaged, the central canal (cc) is labeled for orientation. FIG. 1B Assessment of visible Fluorogold diffusion in the control treated and immunologically disrupted hemisected spinal cord. Diffusion of the retrograde tracer was measured at the light microscope level at the time points indicated after injection into the lumbar spinal cord (see methods for details). Immunological demyelination did not significantly affect the diffusion of the tracer.

FIGS. 2A–2D show electron photomicrographs of transverse sections through the dorsolateral funiculus after continuous intraspinal infusion of immunological reagents for 7 days. (FIG. 2A) Within one spinal segment (<2 mm) of the infusion site, large regions of naked, demyelinated axons were visible. Some axons were observed to be associated with monocyte cells (M, e.g. infiltrating macrophage) and or endogenous microglia, some of which also contained myelin ovoids (arrow) or myelin debris. (FIG. 2B) On other grids, monocytes and invading polymorphonucleocytes (PMN) could also be seen in close association with demyelinated axons. Macrophages and/or microglia were identified on the basis of their high density endoplasmic reticulum (arrowheads), and "finger-like" processes. Some monocytes have laid down basal lamina components such as collagen (Col), which distinguishes them from astrocytes. Multi-lobednuclei are characteristic of PMNs and facilitate their identification. (FIG. 2C) Example of myelin-disruption. This is often observed 4–8 mm (1–2 spinal segments) from the immunological infusion site where the axons were still associated with myelin; however, the myelin lamellae were disrupted (delaminated). Some regions of coherence in the myelin wrapping did persist (arrows). (FIG. 2D) Example of the appearance of axons within the dorsolateral funiculus after a control infusion of Guinea-pig complement alone. Some non-specific damage of myelin sheathes occurred, especially within one spinal segment of the infusion site; however, the compact nature of the myelin remained intact. Original magnification×4000 (FIGS. A, B, D),×10000 (FIG. C).

Figure 3A:
Figure 3B:
Figure 3C:
Figure 3D:

FIGS. 3A–3G presents demonstrations of regeneration of rubrospinal neurons after left-side thoracic hemisection and subsequent immunological myelin suppression treatment. FIGS. 3A and 3B are photomicrographs of rubrospinal neurons from the same experimentally-treated animal (14 days infusion of serum complement with anti-GalC); FIG. 3A is from the uninjured Red nucleus while B is from the injured Red nucleus. FIGS. 3C and 3D are also from same control-treated animal (14 days infusion of serum complement only): FIG. 3C is the uninjured Red nucleus and FIG. 3D is the injured Red nucleus. Fluorogold injection within the rostral lumbar cord 28 days after injury resulted in the retrograde labeling of uninjured rubrospinal neurons (FIGS. 3A and 3C) as well as those rubrospinal neurons that had regenerated from the injured Red nucleus (FIGS. 3B and 3D). (FIGS. 3E and 3F) Axotomized rubrospinal neurons were retrograde labeled at the time of injury with the first label RDA (solid arrow heads) and subsequently 28 days later with the second label FG (open arrow heads). Double-labeled (RDA+FG) cells are indicated by an asterisk and represent those rubrospinal neurons that had regenerated after immunological myelin-suppression treatment. Scale bar=100 $\mu$m.

Figure 4:
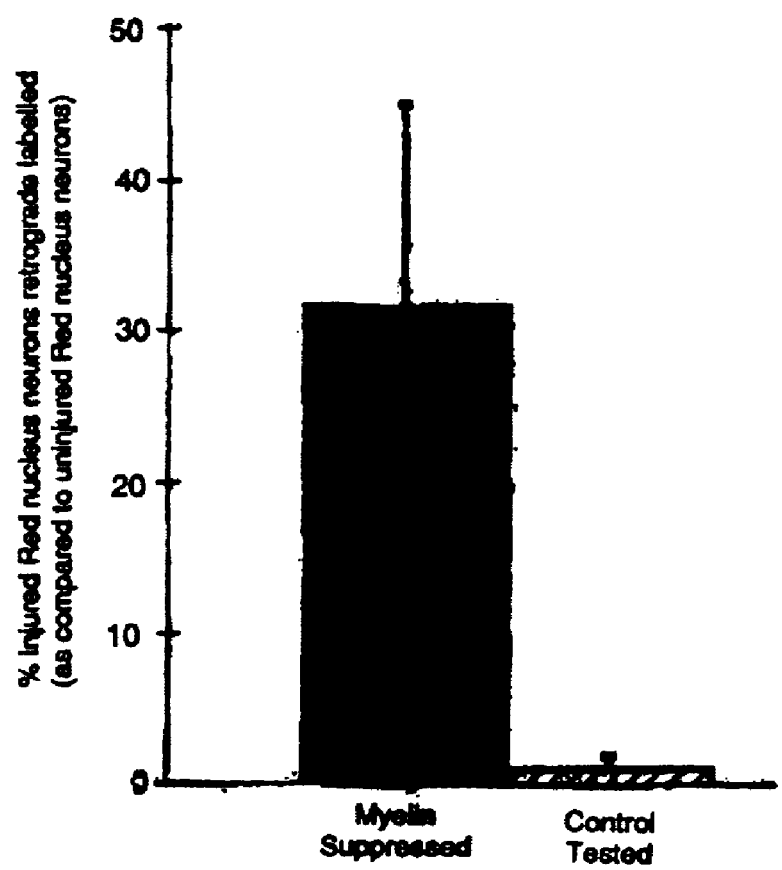

FIG. 4 shows a relative quantitative assessment of regeneration of rubrospinal neurons after thoracic injury and immunological treatment. Regeneration was assessed by counting FG-labeled cells in alternating tissue sections: those with both multipolar neuronal morphology and FG labeling were deemed to be positive. Percentage regeneration was calculated by comparison of the retrograde labeled cell counts from the injured Red nucleus with the control uninjured Red nucleus within the same animal. For each animal, the degree of lesion was assessed. Filled bar: myelin suppressed, hatched bar: pooled control treated groups. Data shown±s.d.

Figure 5A:
Figure 5B:
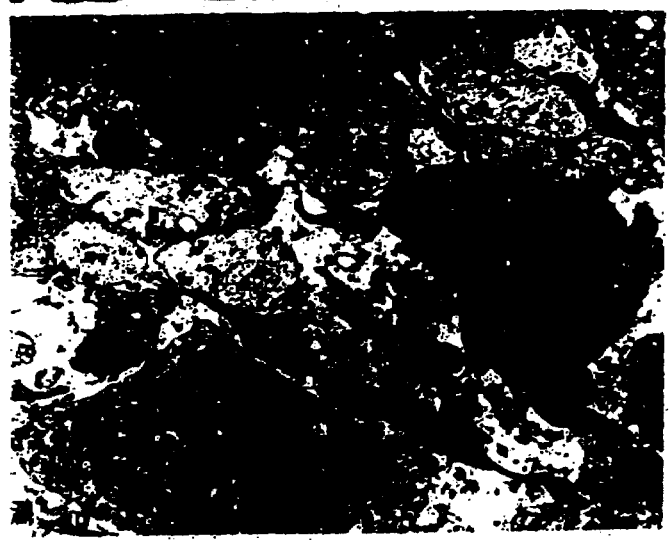
Figure 5C:

FIGS. 5A–5C demonstrates effects of removal of a single complement protein on immunological demyelination. (FIG. 5A) Control uninjured spinal cord. Electron photomicrographs of transverse sections through the dorsolateral funiculus indicating the ultra structure of adult myelin sheaths. (FIG. 5B) 7 day infusion with myelin-specific antibody and human complement sera results in a profound myelin suppression. (FIG. 5C) The removal of the C3 component of complement results in a lack of myelin-removal, indicating the fundamental role of this protein in either (i) opsonization, or (ii) the propagation of the cascade to the lytic membrane attack complex (MAC), the final lytic pathway complex. It is believed that itis a fundamental and essential requirementofamyelin specific cell surface binding antibody to activate the classical complement pathway for effective transient demyelination.

Figure 6:
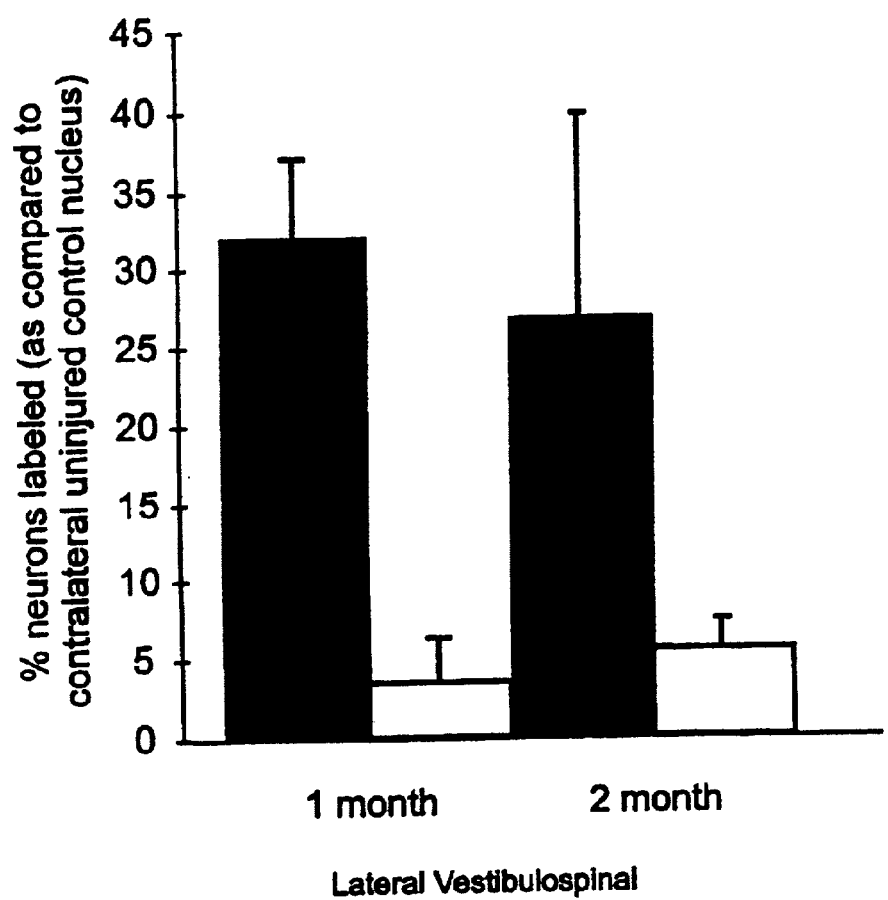

FIG. 6 shows a relative quantitative assessment of regeneration of lateral vestibulospinal neurons after thoracic injury and delayed immunological treatment. Immunological demyelination treatment was delayed for 1 or 2 months after injury as indicated. Regeneration was assessed by counting FG-labeled cells in alternating tissue sections: those with both multipolar neuronal morphology and FG labeling were deemed to be positive. Percentage regeneration was calculated by comparison of the retrograde labeled cell counts from the injured lateral vestibulospinal nucleus with the control uninjured lateral vestibulospinal nucleus within the same animal. For each animal, the degree of lesion was assessed. Filled bar: myelin suppressed, open bar: pooled control treated groups. Data shown±s.d.

FIG. 7A presents a drawing-of a dorsal view of the rat central nervous system, indicating the relative origins and course of the rubrospinal tract (RN) and lateral vestibular tract (LVe). Also illustrated (solid line) is the left-side thoracic hemisection lesion (~T10, line), the immunological infusion site (~T11, vertical hatching), and the site of the Fluorogold injection (~L1, diagonal hatching). FIG. 7B is a composite photomicrograph of parasagittal sections through the lower thoracic and rostral lumbar spinal cord (T9-L1, rostral is up). Some Fluorogold diffusion can be clearly emanating from the injection site as an intense white "halo", however, this staining rapidly decreased with distance from the site of injection and none was ever visible rostral to T11, the immunological infusion site (i.e. no diffusion to or above the lesion at T10, thus no evidence for any "false" positive retrograde labeling of brainstem-spinal projections). FIG. 7C is a photomicrograph of a transverse section of spinal cord at the level of T10 left side hemisection lesion, stained with cresyl violet. All lesions were assessed and always resulted in severing the funiculi through which the rubrospinal and lateral vestibulospinal tracts traverse. The contralateral dorsal (dh) and ventral (vh) horns were always left undamaged; the central canal (cc) is labeled for orientation. FIGS. 7D and 7E show non-specific fluorescence associated with blood cells within the lesion and pump implantation sites indicating the degree of damage associated with the lesion and cannula implantation, respectively. Specific Fluorogold fluorescence labeling was never observed at the level of the cannula implantation or hemisection injury.

FIGS. 8A–8E show regeneration of lateral vestibulospinal neurons after left-side thoracic hemisection and subsequent immunological myelin suppression treatment. FIGS. 8A and 8B are photomicrographs of lateral vestibulospinal neurons from the same experimentally-treated animal (14 days infusion of serum complement with anti-GalC); FIG. 8A is of the injured lateral vestibular nucleus and B is from the uninjured lateral vestibular nucleus and. FIGS. 8C and 8D are also from same control-treated animal (14 days infusion of serum complement only); where FIG. 8C is the injured lateral vestibulospinal nucleus and FIG. 8D is the uninjured lateral vestibulospinal nucleus. Fluorogold injection within the rostral lumbar cord 28 days after injury resulted in the retrograde labeling of uninjured lateral vestibulospinal neurons (FIGS. 8B and 8D) as well as those lateral vestibulospinal neurons that had regenerated from the injured lateral vestibulospinal nucleus (FIGS. 8A and 8C), please see results for further details. FIG. 8E is a drawing of a transverse section through the midbrain indicating the location of the lateral vestibular nucleus (LVe), SpVe=spinal vestibular nucleus, MVe=medial vestibular nucleus, $4V=4^{th}$ ventricle, FN=facial nerve tract, $7=7^{th}$ cranial (facial) nucleus, PFl=paraflocculus. Scale bar= 100 $\mu$m.

Figure 9:
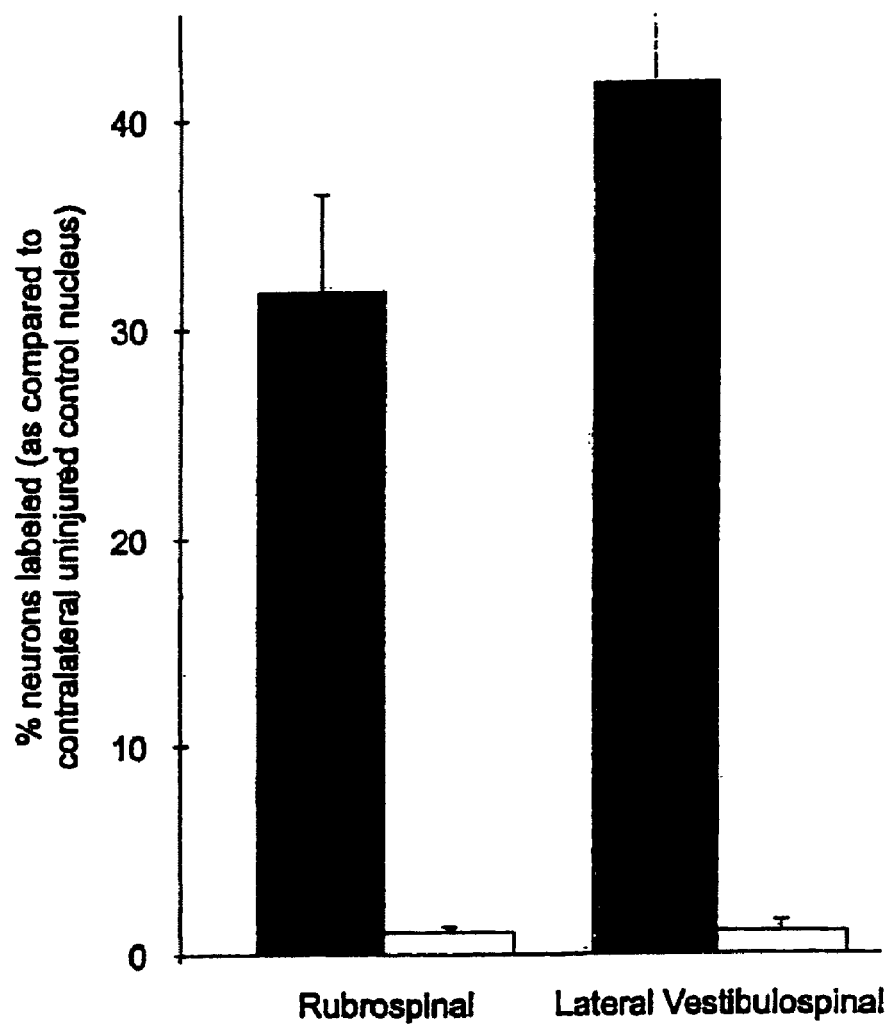

FIG. 9 shows relative quantitative assessment of regeneration of rubrospinal and lateral vestibulospinal neurons after thoracic injury and immunological treatment. Regeneration was assessed by counting FG-labeled cells in alternating tissue sections; those with both multipolar neuronal morphology and FG labeling, were deemed to be positive. Percentage regeneration was calculated by comparison of the injured nucleus with the contralateral (uninjured) nucleus within the same animal. For each animal the degree of lesion was assessed. Filled bars, experimental, open bars, pooled control groups.

Figure 10:
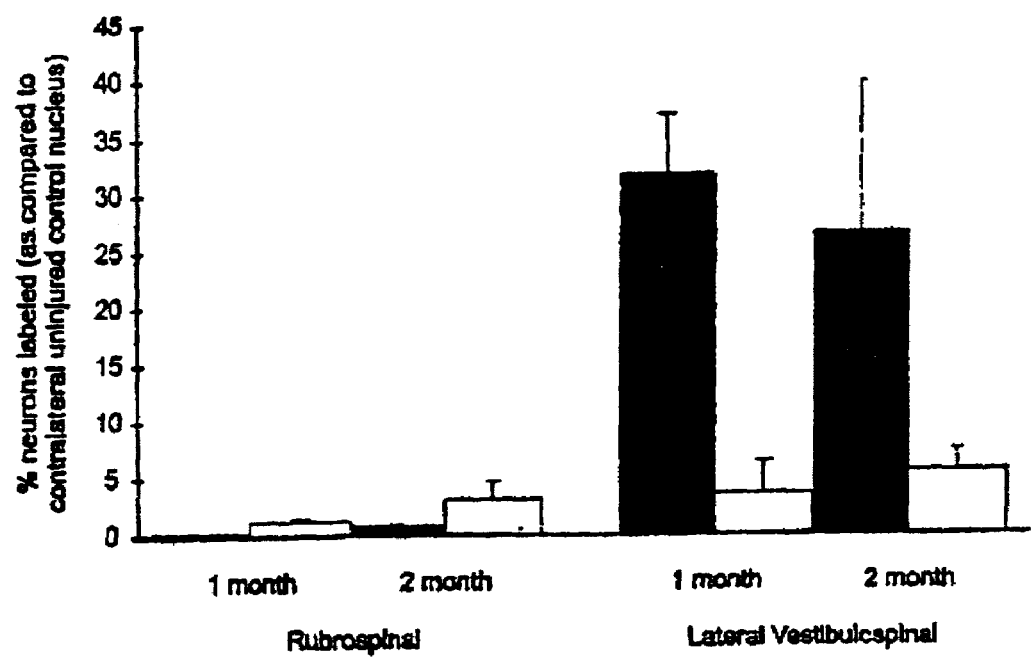

FIG. 10 shows a quantitative assessment of regeneration of descending brainstem-spinal axons after chronic lateral hemisection & delayed immunological treatment. Percentages of retrogradely labeled red nucleus (red) and lateral vestibular (green) neurons vs. Contralateral uninjured, after control (PBS, Ab, GpC) treatment (open bars) or immunological disruption/demyelination (filled bars). Expressed as percentage labeled cells in the injured nucleus vs. Uninjured contralateral.

DETAILED DESCRIPTION OF THE INVENTION

The following terms and abbreviations are used throughout the specification and in the claims:

The term "antibodies or fragments thereof" includes recombinant, chimeric, and affinity modified forms made by techniques of molecular biology well known in the art;

"CNS" refers to the central nervous system;

The term "complement protein or fragment thereof" (C) refers to any of 13 whole serum proteins or any of more than 20 intermediates and complexes of the complement system, the primary humoral mediator of antigen-antibody reactions, and includes variants, analogs, and chemical derivatives thereof;

The term "composition" is used to indicate more than one component. The elements of the composition can be mixed together, however, it is not necessary that they be combined in the same solution. In an alternative embodiment, they do not need to be packaged, stored or even mixed together. The elements (antibody-type and complement-type) can be delivered to the site of nerve damage sequentially, or at the same time. The need for a therapeutically effective temporal sequence is understood by one skilled in the art. The concept of at least one complement fixing antibody or fragment thereof, plus at least complement protein or active fragment thereof equates with the concept of the composition. These elements are delivered to the site of damage to form a complex with an appropriate epitope present in myelin to be transiently demyelinated. Thus, the first two types of elements (of which there can be more than one member of each type of element, for example, two or more antibody or component proteins or fragments) are delivered to the site targeted for transient demyelination to form a complex in situ in vivo with the epitope(s) on myelin.

The term "demyelination" refers to the removal or breakdown of myelin in neurological tissue. Demyelination consists of the removal of the myelin sheath, such as that surrounding neurons or neuronal projections (e.g., the axons). This process may be chemical or immunological in both the experimental and pathological states. This invention effects transient demyelination in order to promote repair and regrowth.

The term "disruption" refers to delamination or disruption of the three-dimensional conformation of myelin;

The term "dysfunction" when used to describe the therapeutic use of the invention encompasses any type of trauma to the nervous system and resulting loss of function. Such trauma can arise from either physical injury or disease;

The term "Fab" means an antibody fragment that is obtained by cleaving an antibody in the hinge region yielding two Fab fragments, each having the heavy and light chain domains of the antibody, along with an Fc region;

The term "Fc" means the constant region of the antibody, which may activate complement;

The term "Fv fragment" means a heterodimer of the heavy and light chain variable domain of an antibody. These variable domains may be joined by a peptide linker or by an engineered disulphide bond;

Growth factors are extracellular polypeptide signaling molecules that stimulate a cell to grow or proliferate. Examples are epidermal growth factor (EGF) and platelet-derived growth factor (PDGF). Most growth factors have other actions besides the induction of cell growth or proliferation. Growth factors can be divided into broad- and narrow-specificy classes. The broad-specificity factors, like PDGF and EGF affect any classes of cells. At the opposite extreme lie narrow-specificity factors. In intact animals proliferation of mot cell types depends on a specific combination of growth factors rather than a single growth factor. Thus a fairly smal number of growth factor families may serve, in different combinations, to regulate selectively the prolifertion of each of the many types of cells in a higher animal.

Fibroblast Growth Factor (FGF) is any one of a group of proteins, usually intracellular, that have important angiogenic function and enhance would healing and tissue repair. Over-activity of these factors has been associate with neoplasia.

Neurotrophic factors are a family of substances that promote growth and regeneration of neurons.

While growth factors elsewhere in the body promote and support cell division, neurons cannot divide; but they can regenerate after injury and neurotrophic factors promote this regeneration. They also promote the growth of axons and dendrites, the neuron branches that form connections with other neurons.

"GalC" refers to galactocerebroside;

"MAG" refers to myelin-associated glycoprotein;

"MBP" refers to myelin basic protein;

"MOG" refers to myelin oligodendrocyte glycoprotein;

The term "neurological tissue" refers to neurons and other cells typically situated in the region of the nervous system, such as the spinal cord of the CNS;

"PNS" refers to the peripheral nervous system;

The term "recombinant antibodies or fragments thereof" collectively includes chimeric or recombinant forms of the antibodies or fragments thereof wherein the Fc domain is substituted for an Fc domain of another species or isotype, affinity modified forms of the antibodies or fragments thereof wherein the binding sites are altered, avidity modified forms of the antibodies or fragments thereof wherein the hinge regions are altered, immunoreactive fragments thereof, and combinations thereof; and The term "regeneration of neurological tissue" includes the regrowth of neurons that results in the reformation of neuronal connections, both anatomically and/or functionally.

The present invention resides in the unexpected discovery that a combination of both antibody, which binds an epitope on a myelin-producing glial cell, and complement can be used for disruption and demyelination of the myelin sheath, such that repair and regeneration of mammalian neurological tissue is enhanced. The composition of this invention is valuable as a therapeutic agent in cases in which there is injury or disease of the mammalian nervous system such that there is a need to facilitate neuronal plasticity and the regrowth of neural connections. The neurological tissue is exposed to the myelin disrupting composition, according to the invention, as soon as possible following the injury, trauma, or disease. The nature of the protocol to effect transient demyelination can be determined from Kierstead and Blakemore, 1997, J. Neuropath. Expt. Neurol. 56:1191–1201; Kierstead et al., 1998, Glia, 22:161–170.

The present invention provides compositions and methods of their use for promoting regeneration of neurological tissue in a mammalian subject, such as a human, with a nervous system dysfunction by contacting the neurological tissue with a therapeutically effective amount of a composition comprising a complement fixing antibody, which binds to myelin, and complement. Uses of the composition in the field of veterinary medicine are also an embodiment of the present invention.

The compositions of the present invention are comprised of one or more antibodies or fragments thereof, which bind myelin, and one or more serum complement proteins or fragments thereof.

Antibodies

The antibodies used in this invention can be any antibodies or fragments there of that specifically bind to myelin, wherein said antibodies activate the complement system. The preferred antibodies of the present invention specifically bind a myelin sheath epitope such as galactocerebroside (GalC), O4, Myelin Oligodendrocyte Glycoprotein (MOG), or Myelin Associated Glycoprotein (MAG). Other preferred epitopes are NOGO (formerly NI 35/250) and NI220 and arretin.

Generation of Antibodies

The antibodies of the present invention, or fragments thereof, can be:

a) naturally occurring;

b) antibodies obtained from disease states such as B-cells from multiple-sclerosis patients;

b) produced by recombinant DNA technology;

c) produced by biochemical or enzymatic fragmentation of larger molecules;

d) produced by methods resulting from a combination of a) to c); or e) produced by any other means for producing antibodies.

Human antibodies can be generated by a number of techniques known to those skilled in the art, including the use of insect cells and transgenic plants such as tobacco or corn seed (Cramer, C. L., Crop Tech Development Corp; Reno, J., NeoRx—IVC's IV Annual Conference: Sep. 9–12, S. F., U.S.A.)

The antibodies of the present invention can also be made by traditional technqiues such as monoclonal or polyclonal, although monoclonal antibodies are preferred. In general, antibodies may be obtained by injecting the desired immunogen into a wide variety of vertebrates or invertebrates in accordance with conventional techniques. While rodents, particularly mice, are preferred, other species may be employed, such as members of the bovine, ovine, equine, porcine, or avian families. Immunization of these animals can be readily performed and their lymphocytes, particularly splenocytes, may be obtained for fusions.

Immunization protocols are well known and can vary considerably yet remain effective (Goding, *Monoclonal Antibodies: Principles and Practice* (2nd ed.) (Academic Press, 1986). Isolated proteins, synthetic peptides, and bacterial fusion proteins which contain antigenic fragments of the myelin molecule may be used as immunogens. Preferably the immunogen of peptides or recombinant proteins will be enriched for proteins or fragments thereof containing the epitopes to which antibody-producing B cells or splenocytes are desired.

Once the proteins or peptides thereof have been purified to the extent desired, they may be suspended or diluted in an appropriate physiological carrier for immunization, or may be coupled to an adjuvant. Immunogenic amounts of antigenic preparations enriched in myelin, or antigenic portions thereof, are injected, generally at concentrations in the range of 1 ug to 100 mg/kg of host. Administration may be by injection, such as intramuscularly, peritoneally, subcutaneously, or intravenously. Administration may be one or a plurality of times, usually atone to four week intervals.

Immunized animals are monitored for production of antibody to the desired antigens, then the spleens are removed and splenic B-lymphocytes isolated and fused with a myeloma cell line or transformed. The B-lympocytes can also be isolated from the blood. The transformation or fusion can be carried out in conventional ways, the fusion technique being described in an extensive number of patents, such as U.S. Pat. Nos. 4,172,124, 4,350,683; 4,363,799; 4,381,292, and 4,423,147. The manner of immortalization is not critical, but the most common method is fusion with a myeloma fusion partner. Other techniques of immortalization include EBV transformation, transformation with bare DNA, such as oncogenes or retroviruses, or any other method that provides for stable maintenance of the cell line and production of monoclonal antibodies. The general process for obtaining monoclonal antibodies has been described (Kohler and Milstein (1975) *Nature* 256:495–497). Human monoclonal antibodies may be obtained by fusion of the spleen cells with an appropriate human fusion partner, such as WI-L2, described in European Application No. 82.301103.6. A detailed technique for producing mouse X-mouse monoclonal antibodies has been taught (Oi and Herzenberg (1980) in Mishell and Shiigi (eds.) *Selected Methods in Cellular Immunology* 351–372). The resulting hybridomas are screened to isolate individual clones, each of which secretes a single antibody species to the antigen.

The immortalized cell lines may be cloned and screened in accordance with conventional techniques, and antibodies in the cell supernatants detected that are capable of binding to myelin. The appropriate immortalized cell lines may then be grown in vitro or injected into the peritoneal cavity of an appropriate host for production of ascites fluid. Immortalized hybridoma cell lines can be readily produced from a variety of sources. Alternatively, these cell lines may be fused with other neoplastic B-cells, where such other B-cells may serve as recipients for genomic DNA coding for the antibody.

The monoclonal antibody secreted by the transformed or hybrid cell lines may be of any of the classes or subclasses of immunoglobulins, such as IgM, IgD, IgA, $IgG_{1-4}$, or IgE. As IgG is the most common isotype utilized in diagnostic assays, it is often preferred.

To circumvent the possible antigenicity in a human host of a monoclonal antibody derived from an animal other than human, chimeric antibodies may be constructed. For example, the antigen binding fragment of an immunoglobulin molecule (variable region) may be connected by peptide linkage to at least part of another protein not recognized as foreign by humans, such as the constant portion of a human immunoglobulin molecule. This can be accomplished by fusing the animal variable region exons with human kappa or gamma constant region exons. Various techniques are known to the skilled artisan, such as those described in PCT 86/01533, EP 171496, and EP 173494.

As an alternative method of producing antibodies, U.S. Pat. No. 5,627,052 describes methods of producing proteins that replicate the binding characteristics and desired function of particular antibodies. An example of application of this method includes the isolation and characterization of a human B-lymphocyte cell, producing a specific anti-myelin antibody, for example from the blook of a patient with Multiple Sclerosis.

Antibody Engineering

The antibodies may be used intact, or as fragments, such as Fv, Fab, and $F(ab')_2$ as long as there is an Fc region present to bind complement. Such antibody fragments provide better diffusion characteristics in vivo than the whole antibody, due to their smaller size. The means for engineering antibodies by recombinant DNA and chemical modification methods are considered well-known in the art.

The antibodies may be fragmented to obtain highly immunoreactive $F(ab')_2$, F(ab'), and Fab fragments using the enzyme pepsin by methods well known in the art (see Colcher et al., (1983) *Cancer Res.* 43:736–742).

Due to the development of molecular cloning technqiues, it is now possible to produce human monoclonal antibody fragments quickly by paning phage display libraries against predefined antigenic specificities. For exemplary techniques see: Pistillo et al., Human Immunology, 57(1): 19–26, 1997 Sep. 15).

Antibodies or fragments thereof are also made into recombinant forms by techniques of molecular biology well known in the art (see Rice et al., (1982) *Proc. Natl. Acad. Sci. USA* 79:7862–7865; Kurokawa et al., (1983) *Nucleic Acids Res.* 11:3077–3085, Oi et al., (1983) *Proc. Natl. Acad. Sci. USA* 80:825–829, Boss et al., (1984) *Nucleic Acids Res.* 12:3791–3806; Boulianne et al., (1984) *Nature (London)* 312:643–646; Cabily et al., (1984) *Proc. Natl. Acad. Sci. USA* 81:3273–3277; Kenten et al., (1984) *Proc. Natl. Acad. Sci. USA* 81.2955–2959; Liu et al., (1984) *Proc. Natl. Acad. Sci. USA* 81:5369–5373; Morrison et al., (1984) *Proc. Natl. Acad. Sci. USA* 81:6851–6855; Neuberger et al., (1984) Nature (London) 312 604–608; Potter et al., (1984) *Proc. Natl. Acad. Sci. USA* 81:7161–7165; Neuberger et al., (1985) *Nature (London)* 314:268–270, Jones et al., (1986) Nature (London) 321:522–525; Oi et al., (1986) *BioTechniques* 44:214–221; Sahagan et al., (1986) *J. Immunol.* 137:1066–1074; Sun et al., (1986) *Hybridoma* 5 (Supp. 1): S17–S20; and Sun et al., (1987) *Proc. Natl. Acad. Sci. USA* 84:214–218).

More specifically, the antibodies and fragments thereof may be altered to a chimeric form by substituting antibody fragments of another species, e.g., human constant regions (Fc domains) for mouse constant regions by recombinant DNA techniques known in the art as described in the above cited references. These Fc domains can be of various human isotypes, i.e., IgG, $IgG_2$, $IgG_3$, $IgG_4$, or IgM.

In addition, the antibodies and fragments thereof may be altered to an affinity modified form, avidity modified form, or both, by altering binding sites or altering the hinge region using recombinant DNA techniques well known in the art as described in the above cited references.

The recombinant antibody forms may also be fragmented to produce immunoreactive fragments $F(ab')_2$, F(ab'), and Fab in the same manner as described.

Antibody fragments may also include Fv fragments, the smallest functional modules of antibodies required to maintain the binding and specificity of the whole antibody. Fv fragments are heterodimers composed of a variable heavy chain and a variable light chain domain. Proteolytic digestion of antibodies can yield isolated Fv fragments, but the preferred method of obtaining Fvs is by recombinant technology (See Skerra and Pluckthun (1988) *Science* 240: 1038–1041).

Fvs can be noncovalently-associated $V_H$ and $V_L$ domains, although these tend to dissociate from one another. Stable Fvs can be produced by making recombinant molecules in which the $V_H$ and $V_L$ domains are connected by a peptide linker so that the antigen-combining site is regenerated in a single protein. These recombinant molecules are termed single chain Fvs (scFvs). The means for preparing scFvs are known in the art (See: Raag and Whitlow (1995) *FASEB* 9:73, Bird et al., (1988) *Science* 242:423–426; Huston et al., (1988) *Proc. Natl. Acad. Sci. USA* 85:5879–5883). Alternatively, the two variable domains may be joined and stabilized by an engineered disulphide bond; these are termed disulfide Fvs (dsFvs) (Reiter and Pastan (1996) *Clin. Cancer Res.* 2:245–252).

The Fc domain of an antibody is required for the activation of complement. Fv fragments, which lack the Fc domain, cannot activate complement. In order for Fv fragments to be useful in the present invention, they would have to be designed with a novel activator of the complement cascade. As an example, the Fv fragment could be designed to include the $C_H2$ domain of an IgG antibody. As an alternative example, a wholly synthetic molecule may be linked to the Fv fragment to activate complement, or an activator of complement familiar to those in the field may be linked to the Fv fragment.

The antibody may also be modified by the addition of such molecules as polyethylene glycol (as described in U.S. Pat. No. 5,766,897) as to prolong its biological half-life, potency, or the diffusion of the molecule in situ (U.S. Pat. No. 5,747,446, Chinol et al., 98 Brit. J. Cancer, 78:189–197; Francis et al., 98, Intl J. Hematol. 68:1–18).

Labeling of Antibodies or Fragments:

The antibodies of this invention, or fragments thereof, may be used without modification or may be modified in a variety of ways, for example, by labeling. Labeling is intended to mean joining, either covalently or non-covalently, a label which directly or indirectly provides for a means of detection of the antibody to enable monitoring of the progress of therapeutic treatment using the composition.

A label can comprise any material possessing a detectable chemical or physical property. A wide variety of labels is known, including radionuclides, enzymes, enzyme substrates, enzyme cofactors, enzyme inhibitors, ligands (particularly haptens), fluorescers, chromophores, luminescers, and magnetic particles. These labels are detectable on the basis of either their own physical properties (eg., fluorescers, chromophores and radioisotopes), or their reactive or binding properties (eg., enzymes, substrates, cofactors and inhibitors). These materials are well known to one skilled in the art. U.S. Pat. No. 4,671,958 teaches methods that can be used for labelling antibodies or attaching complement to antibodies.

Complement

The complement portion of the composition may be comprised of one or more complement proteins, fragments, variants, analogs, and/or chemical derivatives.

A fragment of a complement protein refers to any subset of the C molecule. For example, fragments of C3 include C3b, iC3b, C3a, C3c, C3dg, and C3d.

A "variant" of a complement protein or fragments thereof refers to a molecule substantially similar to either the entire protein or a fragment thereof, which possesses biological activity that is substantially similar to a biological activity of the complement protein or fragments thereof. A molecule is said to be "substantially similar" to another molecule if both molecules have substantially similar structures or if both molecules possess a similar biological activity.

Variants of C3b, for example, include C3b dimers, and higher oligomers. When C activation occurs at the cell-surface, multiple cycles of enzyme reactions result in the deposition on the surface of C3b in multimeric form. C3b dimers or higher oligomers indeed have higher affinity for the cell than do C3b monomers.

Variants of complement protein or fragments thereof are produced by chemical or recombinant means well-known in the art. Such variants include, for example, deletions from, or insertions or substitutions of, amino acid residues within the amino acid sequence. For example, at least one amino acid residue may be removed and a different residue inserted in its place. Substantial changes in functional or immunological properties are made by selecting substitutions that are less conservative, ie. that differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. The substitutions that in general are expected to induce greater changes are those in which (a) glycine and/or proline is substituted by another amino acid or is deleted or inserted, (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions, insertions, and substitutions are not expected to produce radical changes in the characteristics of the protein molecule; however, when it is difficult to predict the exact effect of the substitution, deletion, or insertion in advance of doing so, one skilled in the art will appreciate that the effect will be evaluated by routine screening assays. For example, a change in the immunological character of the protein molecule, such as binding to a given antibody, is measured by an immunoassay such as a competitive type immunoassay.

An "analog" of a complement protein or fragment thereof refers to a non-natural molecule substantially similar to either the entire protein or a fragment thereof.

A "chemical derivative" of a complement protein or fragment thereof contains additional chemical moieties that are not normally part of the protein or fragment. Covalent modifications of the peptides are included within the scope of this invention. Such modifications may be introduced into the molecule by reacting targeted amino acid residues of the peptide with organic derivatizing agents that are capable of reacting with selected side chains or terminal residues, as is well-known in the art (T. E. Creighton *Proteins: Structure and Molecule Properties* (San Francisco: W. H. Freeman, 1983) at 70–86).

The complement portion of the composition may be a physically distinct component from the antibody component. Alternatively, the complement proteins or fragments thereof, may be covalently or noncovalently attached directly to the antibody component, such that binding of the antibody to the surface of the myelin triggers the endogenous immune system attack.

The complement components may be fractions that have been purified as well as those that have been enriched in the proteins which comprise the complement system. Such preparations should take into account the relative lability of complement and provide a sufficient combination of factors to allow complete activation of the complement cascade to allow transient demyelination to occur.

The complement portion of the composition may be comprised of one or more complement proteins, fragments, variants, analogs, and/or chemical derivatives. It should be noted, however, that the C3 component of complement plays a fundamental role either in opsonization or in the propagation of the cascade to the lytic MAC. In a preferred embodiment, the C3 component or a fragment, variant, analog, or chemical derivative thereof should be included in the complement portion of the composition. In situations targeted for demyelination, the C3 component should certainly be present for optimal results. In situations targeted for regeneration it is less certainty required.

The complement portion of the composition may be derived from a subject's own serum, from the serum of a donor, or from the pooled sera of a number of donors, such as those available commercially, which are produced to consistent, approved standards.

The complement components may be derived from species different from that species to which it is administered due to the fact that the compositions are introduced directly to the neural tissue (e.g., intrathecally).

Other Factors

The composition may optionally include other chemicals or drugs such as growth factors and neurotrophins. It is known that the beneficial effects of blocking CNS myelin-associated inhibitors on axonal regeneration can be augmented by the concomitant application of neurotrophins, such as NT-3 (Bregman et al., (1995) *Nature* 378:498–501, Schnell et al., (1994) *Nature* 367:170–173). FGF-1 can also be used (Chang et al., 1996, supra).

In a preferred embodiment, the composition is comprised of a GalC-specific monoclonal antibody and human serum complement.

In another preferred embodiment, the composition is comprised of a MOG-specific monoclonal antibody and human serum complement.

Uses

The compositions of the present invention can be used to promote regrowth, repair, and/or regeneration of neurons in the CNS of a subject by stimulating transient immunological disruption of myelin or transient demyelination of axons. Preferably, the transient demyelination process of the present invention occurs in the CNS, most preferably in the spinal cord.

The subject may be any mammal. In a preferred embodiment, the subject is human.

The compositions of the present invention can be used to promote regrowth, repair, and/or regeneration of dysfunctional neurons in the CNS that have been damaged as a result of injury, such as a spinal cord injury. The method can be used following immediate or chronic injury.

The compositions of the present invention can also be used to promote regrowth, repair, and/or regeneration of dysfunctional neurons in the CNS that have been damaged as a result of disease, such as degenerative diseases including Alzheimer's and Parkinson's disease.

The compositions of the present invention can also be used to generate an environment within the mammalian CNS that is relatively permissive to growth of transplanted cells. For example, if PNS cells are transplanted into a site in the CNS that has been damaged, axons will be able to grow into the transplanted tissue but will be unable to grow out of this tissue back into the CNS due to the inhibitory effects of myelin. The compositions of the present invention can be used to disrupt the myelin in the CNS to allow the axons to extend into this area.

Preparations and Administration

Methods of using the compositions of the present invention comprise administering a therapeutically effective amount of such a composition to the subject. As used herein, the term "therapeutically effective amount" refers to an amount of composition sufficient to effectively and transiently disrupt and/or demyelinate the CNS so that repair and regeneration of neurological tissue and neuronal connections is enhanced. Generally, the therapeutic composition is administered at a range from about 0.03 mg antibody to about 0.6 mg antibody in a 20% to 30% complement solution per kg body weight. Preferably, the range is from 0.05 mg antibody to 0.4 mg antibody in a 20% to 30% complement solution per kg body weight. Most preferably, the range is from 0.1 mg antibody to 0.3 mg antibody in a 20% to 30% complement solution per kg body weight. The exact ratio of antibody to complement will vary depending on the circumstances; however, since the amount of complement activated is directly proportional to the number of bound antibody molecules, it is possible to administer relatively high concentrations of complement in excess of the relative concentration of antibody. In addition, the particular concentration of antibody administered will vary with the particular dysfunction and its severity, as well as with such factors as the age, sex, and medical history of the patient. Those of skill in the clinical arts will know of such factors and how to compensate the dosage ranges of the composition accordingly.

The majority of spinal cord injuries result from damage to the vertebral column surrounding the spinal cord. This damage includes fractures, dislocations, or both. Much of the damage to the spinal cord is due to secondary phenomena that occur within hours following the injury. At this point, the resultant damage may be reversible; consequently, a critical factor for recoverable CNS function is the amount of time that evolves between injury and the institution of therapy. Most preferably, when the nervous system dysfunction is a result of injury, administration of the composition to the subject will be as close in time to the time of the injury as possible.

A composition according to the method of the invention can be administered to a subject parenterally by injection or by gradual infusion over time. For example, the composition can be administered intrathecally or injected directly into the spinal cord.

Preparations for parenteral administration are contained in a pharmaceutically acceptable carrier that is compatible with both the components of the composition and the patient. Such carriers include sterile aqueous or non-aqueous solutions, suspensions, and emulsions. Examples of non-aqueous solvents include propylene glycol, polyethylene glycol, metabolizable oils such as olive oil or squalane, and injectable organic esters such as ethyl oleate. Aqueous carriers include water, alcoholic/acqueous solutions, and emulsions or suspensions, including saline and buffered media. Parenteral vehicles include sodium chloride solution, Ringer's dextrose, dextrose and sodium chloride, lactated Ringer's, or fixed oils. Preservatives and other additives may also be present such as, for example, antimicrobials, antioxidants, chelating agents, and inert gases and the like. A preferred carrier is artificial cerebrospiral fluid.

Kit

The materials for use in the method of the invention are ideally suited for the preparation of a kit. Such a kit may comprise a carrier means compartmentalized to receive in close confinement one or more container means, such as vials, tubes, and the like, each of the container means comprising one of the separate elements to be used in the method. For example, one of the container means may comprise a GalC-specific antibody. Alternatively, the antibody and complement may be present in the same container. The constituents may be present in liquid or lyophilized form, as desired. Needles and/or other equipment that facilitates delivery of the complement and antibody to the site of damage may include:

a) silastic, Polyethylene, Tygon (Norton Performance Plastics) tubing, b) subcutaneous pumps, (such as the Medtronic pump system known for the administration of baclofen intrathecally), c) spinal needle for direct intraspinal administration, or for short-term intrathecal administration.

One example of a method using such a kit can be described as, a 14-gauge Tuohy needle is inserted into the lumbar subarachnoid space. A 5-F catheter is coaxially placed with the tip at L10 and tunneled to the flank (or appropriate location). This type of instruction would be understood by one familiar with the technique. Tubing is placed intrathecally, and connected to the pump. The pump, containing a finite folume of the reagents is placed under the skin this can be refilled in the Doctor's office, via a needle inserted into a septa in the pump. Or the Infusaid pump may be used in the alternative.

Advantages Over Current Methods

The compositions and their uses of the present invention have a number of advantages over methods currently available for the regeneration of neuronal growth in the CNS.

Interventional therapies, including opiate antagonists, thyrotropin-releasing hormone, local cord cooling, dextran infusion, adrenergic blockade, corticosteroids, and hyperbaric oxygen, are targeted at reducing secondary inflammatory damage after atraumatic injury to the spinal cord in order to prevent the spread of damage to uninjured neurons. Unlike the present invention, however, they do not promote regeneration of the damaged neurons.

Peripheral nerve transplants and the grafting of donor cells into the CNS are useful in that axons can grow into them, however, the axons cannot grow out of them into the surrounding CNS due to the inhibitory myelin present. In contrast, the present invention disrupts the inhibitory myelin to allow regrowth of neurons in the CNS.

The present invention is described in further detail in the following non-limiting examples. It is to be understood that the examples described below are not meant to limit the scope of the present invention. It is expected that numerous variants will be obvious to the person skilled in the art to which the present invention pertains, without any departure from the spirit of the present invention. The appended claims, properly construed, form the only limitation upon the scope of the present invention.

EXAMPLE I

The following example illustrates that the transient developmental suppression of myelination or the disruption of mature myelin by local intraspinal infusion of serum complement proteins along with a complement-fixing, myelin-specific antibody facilitates brainstem-spinal axonal regeneration after spinal transection in a mammalian subject.

Materials and Methods:

Surgical Spinal Transection and Transient Immunological Myelin Disruption:

Ten to 12 week old adult female rats (Sprague-Dawley), approximately 200 g in weight, were anaesthetized with Ketamine/Xylazine (60 mg/kg and 7 mg/kg, respectively). After a limited dorsolateral laminectomy at T10, a left-side spinal cord hemisection lesion was made with micro-scissors. The extent of the lesion was then confirmed by passing a sharp scalpel through the lesion site three times (FIG. 1A). Immediately after the lesion, an intraspinal cannula was implanted at T11 (n=22 total) and connected to an Alzet osmotic pump (14 day) to subsequently deliver a continuous intraspinal infusion (@ 0.5 $\mu$l/hr) of serum complement (GIBCO BRL, #19195-015, 33% v/v) along with a complement-fixing IgG antibody to galactocerebroside (either our own polyclonal antibody or Chemicon Intl. Ltd., #AB 142, 25% v/v). Cannulae were held in place by means of dental acrylic applied to the vertebral bone. Muscle layers were then sutured over the dental acrylic, and the superficial tissue and skin were closed. The extent of the hemisection lesion was always confirmed histologically at the end of the 5-week treatment and recovery period.

All control animals received an identical hemisection lesion and were then intraspinally infused via an osmotic pump, for the same time period, with either vehicle alone (0.1 M phosphate buffered saline, PBS, n=5), antibody alone (25% v/v, n=2), or serum complement alone (33% v/v, n=6). All surgical procedures and subsequent animal care protocols were in accordance with Canadian and University of British Columbia Animal Care Committee guidelines.

Electron Microscopy:

Tissue for ultrastructural analysis was obtained from 10–12 week old adult female Sprague-Dawley rats sacrificed 7 days after infusion of serum complement along with a complement-fixing IgG antibody to GalC (see above for details) via an osmotic pump. Animals were lethally anaesthetised with Ketamine/Xylazine (120 mg/kg and 15 mg/kg, respectively), then perfused intracardially with 200 ml of 0.1M PBS (pH 7.4) followed by 100 ml of 4% glutaraldyhyde in 0.1M PB, (pH 7.3) and subsequently postfixed overnight in the same fixative. The infusion site and surrounding cord was cut into 1 mm transverse blocks and processed to preserve rostral-caudal sequence. Blocks were washed in 0.1M sodium cacodylate buffer (24 hours), postfixed in 2% OsO4, dehydrated through ascending alcohols, and embedded in Spurrs' resin according to standard protocols. Tissue blocks from experimental and untreated-control animals were processed in parallel. Thin sections (1 $\mu$m) were cut from each block, stained with alkaline Toluidine Blue, and examined under a light microscope. For electron microscopic examination, blocks were trimmed then sections were cut at 80–100 $\mu$m, mounted on copper grids, stained with uranyl acetate and lead citrate, and viewed under a Ziess EM 10C electron microscope (at 80 kV).

Retrograde Neuronal Labeling:

If a retrograde tracer (single label) is injected into the rostral lumbar cord (1 cm caudal to the injury site), it should be incorporated and transported back to the cell bodies of origin by both intact axons, as well as regenerated projections. Consequently, it is essential that the retrograde tracer reliably and extensively label most, if not all, descending spinal projection neurons. An equally important parameter is that the tracer must be injected in a controlled and reproducible manner at a distance sufficiently caudal to the spinal injury to prevent any direct diffusion of the tracer to the level of the hemisection injury. The retrograde label that best satisfies all these conditions is Fluorogold (Sahibzada, et al., (1987) *Brain Res.* 415:242–256). Fluorescent dextran amines, such as RDA, require a recent axonal injury to facilitate axonal uptake (Heimer and Zaborszky *Neuroanatomical Tract-tracing Methods* 2: *Recent Progress* (New York: Plenum, 1989)), and are therefore better suited for use in the double label retrograde-tracing studies.

Single Label Studies:

Twenty-eight days after the hemisection lesion and, consequently, 14 days after completion of the intraspinal infusion of the immunological reagents, each adult rat was anaesthetized with Ketamine/Xylazine (60 mg/kg and 7.5 mg/kg, respectively). Fluorogold (FG, 100–150 nl total volume, 5% w/v in sterile dH$_2$O; Fluorochrome Inc. Englewood, Colo., USA) was injected (50–75 nl) bilaterally into the middle of the spinal tissue at the L1 level, approximately 1 cm caudal to the lesion site.

The specific effect of the demyelinating protocol on the extent of diffusion of FG was also assessed. Rats (n=8) were experimentally treated as described above, however, animals were killed at 12, 24, 72, and 120 hours after injection of FG into the L1 cord. Eight other rats served as controls, where the pump contained vehicle only, and were processed in parallel with the experimentally treated animals. Cryostat sections (25 µm thick) were analyzed for the extent of FG diffusion from each injection site (FIG. 1B). There were no significant differences in the extent of visible FG diffusion, as detected at the light microscope level between experimentally treated and control treated animals. In all cases the range of FG diffusion was 4–6 mm (1–1.5 spinal segments) from the injection site or at least 1.5 spinal segments caudal to the lesion site.

Double Label Studies:

At the time of lesion, the hemisection site was packed with gel-foam soaked with 12% (w/v in sterile $dH_2O$) rhodamine-conjugated dextran amine (RDA, 10,000 MW FluoroRuby, Molecular Probes) for 30 minutes. The gel-foam was then removed, and the remaining surgical procedures were completed (as outlined above). After 28 days survival, all animals were anaesthetized with Ketamine/Xylazine (60 mg/kg and 7.5 mg/kg, respectively). FG (100–150 nl total volume, 5% w/v in sterile $dH_2O$) was injected (50–75 nl) bilaterally into the spinal parenchyma at the L1 level of the cord (n=6).

Analysis of Axonal Regeneration:

Seven days following the injection of the FG tracer into the lumbar cord, animals were lethally anaesthetised with Ketamine/Xylazine (120 mg/kg and 15 mg/kg, respectively) and then perfused intracardially with 200 ml of 0.1M PBS (pH 7.4) followed by 100 ml of 4% paraformaldehyde in 0.1M PBS, (pH 7.3). The brain and spinal cord were then removed and postfixed overnight in the same fixative. Subsequently, each brain and spinal cord was cleared of fixative and cryo-preserved by placing the tissue in a series of sucrose solutions (15% followed by 21%). Coronal or parasagital sections were cut at 25 µm thickness on a cryostat. The brainstem and spinal cord tissue sections were examined under a Zeiss Axioskop with a 100 W mercury bulb (excitation/emission wavelengths: FG, 365/420 nm; RDA, 546/590 nm).

The brainstem-spinal nucleus used to assess the axonal regenerative abilities of experimentally treated animals was the Red Nucleus (RN, origin is contralateral to the hemisection) Spinal-projecting axons from each RN cross to the opposite side of the midbrain and descend throughout the spinal cord within the contralateral dorsolateral funiculus. This contralateral spinal projection pathway is known to be a completely lateralized tract with the possible exception of 2–5% of the axons, which may project to the cord via an ipsilateral route (Brown (1974) *J. Comp. Neurol.* 154: 169–188, Huisman et al., (1981) *Brain Res.* 209:217–286; Shieh et al., (1983) *J. Comp. Neurol.* 214:79–86. Waldron and Gwyn (1969) *J. Comp. Neurol.* 137:143–154).

Using a single-blind protocol, the number of retrograde labeled neurons within the Red Nucleus (RN) were counted in every other tissue section throughout the nucleus to avoid counting the same neuron twice. Only those cells exhibiting a nucleus and a neuronal morphology (i.e. multi-polar in appearance), and that were specifically labeled with FG (i.e. not visible using other fluorescent filters; see above) extending into the proximal processes, were deemed to be positively labeled spinal-projecting neurons. The percentage of regenerating neurons was then determined in comparison to the number of labeled neurons within the contralateral (uninjured) control nucleus within the same animal.

Figure 2A:
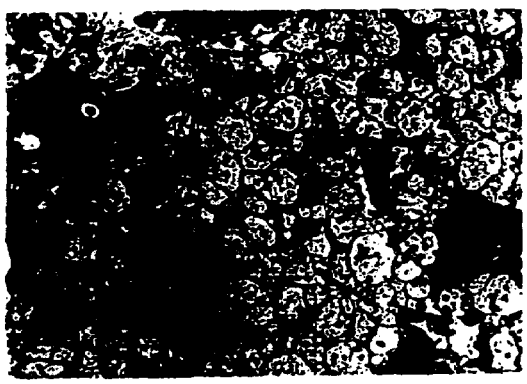
Figure 2B:
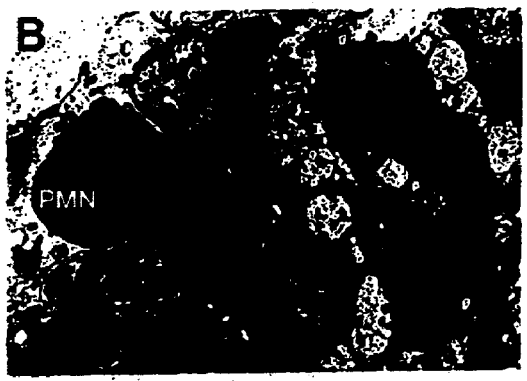
Figure 2C:
Figure 2D:

Results:

Extent of Spinal Cord Demyelination and Myelin Disruption after Immunological Treatment Direct intraspinal infusion of 33% heterologous (guinea pig) serum complement along with polyclonal antibodies to GalC (25%) in PBS over 7 days (@ 0.5 µl/hr) resulted in extensive demyelination up to 2 mm away from the infusion cannula (total rostrocaudal distance of 4 mm or approximately 1 spinal segment (FIG. 2A). This zone of demyelination was bounded on either side by a further 8 mm or 2 segments of spinal cord characterized by disrupted myelin (i.e. myelin that is extensively de-laminated, having an unraveled appearance, FIG. 2C). As shown in previous studies (Keirstead et al., (1995) *J. Neurosci.* 15:6963–6974, Keirstead et al., (1992) *Proc. Natl. Acad. Sci.* (USA) 89:11664–11668, Keirstead et al., (1997) *Brain. Res. Bull.* 44:727–734), control infusions of heterologous serum complement alone, myelin-specific antibody alone, or PBS alone resulted in only limited non-specific damage immediately centered around the cannula site. There was no surrounding zone of demyelination or myelin disruption (FIG. 2D).

The immunological demyelination and disruption of myelin within the experimentally-treated adult rat spinal cord is an active process extending throughout the entire cross-sectional profile of the cord. Immunological myelin disruption commences within 1 day and is associated with an invasion of macrophages or resident microglia and polymorphonuclear cells (e.g. leukocytes such neutrophils, eosinophils and basophils). Many macrophages/microglia contain myelin fragments and complete their phagocytic activity within 7 days (FIG. 2B). This pattern of demyelination and myelin disruption can be maintained for as long as the serum complement and myelin-specific antibody are infused. Recent evidence suggests that after the immunological infusion is terminated, remyelination begins within 2 weeks (Keirstead and Blakemore (1997) *Glia* (In Press), Dyer, Bourque, and Steeves (unpublished observations)); the new myelin originates from differentiating oligodendrocyte progenitors, although invading Schwann cells and surviving "mature" oligodendrocytes may also contribute to remyelination.

Choice of Retrograde Tracer and its Diffusion Distance from the Injection Site

In this study, the major anatomical evidence for axonal regeneration within the hemisected and immunologically myelin-suppressed spinal cord of adult rats depends on a comparison between the number of retrogradely-labeled neurons within a homologous pair of brainstem-spinal nuclei. For these comparisons to be valid, the candidate brainstem spinal nuclei must have highly unilateral projections that are confined to one side of the spinal cord at all levels. A left thoracic hemisection (FIG. 1A) severed the contralaterally-projecting magnocellular neurons of the right red nucleus (RN), but left the projections from the left RN undamaged (as they project through the intact right dorsolateral funiculus of the thoracic cord).

In all cases, the Fluorogold label (100–150 nl) was injected bilaterally within the rostral lumbar cord (1 cm or 3 spinal segments caudal to the hemisection injury site). We assessed the time course and degree of rostrocaudal diffusion of Fluorogold within the lumbar and thoracic spinal cord of normally myelinated (control) animals and experimentally treated rats (i.e. under demyelinated and myelin disrupted conditions). Random 25 μm sections of experimental and control-treated spinal cords (extending from L2 to T8) were examined under a fluorescent microscope using the highest intensity setting of the 100 W mercury lamp. Spinal tissue was examined for the extent of Fluorogold diffusion at varying survival intervals after injection, including: 12 hr (n=4), 24 hr (n=4), 3 d (n=4), and 5 d (n=4). The maximum rostral diffusion distance observed was 4–6 mm (or 1–1.5 spinal segments) and occurred within a time span of 24 h. The degree of Fluorogold diffusion within the lumbar cord did not change over the subsequent time points examined (FIG. 1B).

In summary, no animal (experimental or control) showed any evidence of the Fluorogold label within the spinal cord at the level of the hemisection lesion (T10); thus, by this criteria, no animals had to be excluded from this study. The available evidence indicates that the retrograde label was restricted to labeling intact and regenerating brainstem-spinal neurons having axonal projections caudal to the T10 injury site.

Evidence for Brainstem-Spinal Axonal Regeneration by Retrograde Neuronal Labeling 28 animals (12 experimental (9 retrogradely single-labeled, 3 double-labeled) and 16 control (13 retrogradely single-labeled, 3 double-labeled)) were subjected to a left-side lateral hemisection of the T10 spinal cord. Immediately after hemisection, an infusion cannula (connected to a 14 d osmotic pump) was inserted directly into the spinal cord 4–5 mm (1 spinal segment) caudal to the injury site. The osmotic pump contained one of a number of 3 different control solutions or the experimental treatment (i.e. PBS vehicle alone, serum complement alone, anti-galactocerebroside antibody alone, or serum complement with anti-GalC antibodies, respectively). Animals were then allowed to recover for 28 days before the Fluorogold was injected into the rostral lumbar, 1 cm (i.e. 3 spinal segments) caudal to the lesion site. After a further 7 days survival, each animal was killed, and the brain and spinal cord were removed for examination and analysis (see Materials and Methods for criteria used to determine a labeled neuron).

The extent of the hemisection lesion was assessed in every animal. In all but one experimental and one control-treated animal, the left thoracic spinal cord was hemisected (FIG. 1A). Most importantly, the region of the rubrospinal tract (dorsolateral funiculus) was severed. The right side white matter tracts were always remained intact and undamaged, usually the gray matter of the contralateral side was also undamaged.

Comparing "blind" counts of the number of labeled neurons within each RN (FIGS. 3A–B, Table 1), the data indicated that 31.8%±13.38% (n=9, range 10–50%) of the injured magnocellular RN neurons had regenerated a sufficient distance into the caudal lumbar cord to incorporate and retrogradely transport the Fluorogold (FIG. 4). In contrast, control treated animals, receiving either the PBS vehicle alone, GalC antibody alone, or serum complement alone, did not exhibit a significant amount of RN labeling: 1.49%±0.84%, (FIG. 3C–D; FIG. 4, n=13, range 0–3, Table 1). The labeling of some neurons within the injured right RN nucleus may represent the small number of RN that do not project to the opposite side of the midbrain and descend within the ipsilateral (uninjured) cord (Shieh et al., (1983) *J. Comp. Neurol.* 214;79–86). No retrograde-labeling of cells was observed within the parvocellular region of the RN. This was expected since this RN region predominantly projects only as far as the cervical region of the cord.

Figure 3E:
Figure 3F:
Figure 3G:
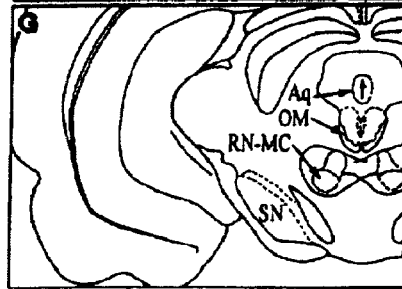

Double retrograde labeling of the injured and myelin-suppressed rubrospinal tract was also qualitatively assessed (FIGS. 3E and F). Large numbers of RDA-positive (first label) magnocellular RN neurons were observed after direct labeling of the lesion site at the time of hemisection injury to the thoracic spinal cord. After intraspinal myelin-suppression and subsequent injection of Fluorogold caudal to the lesion site, a small overlapping population of FG-positive neurons was observed (i.e. some neurons were labeled with both RDA and FG). Cells labeled exclusively by the first or the second tracer were also present in every brainstem analysed. The low number of double labeled brainstem-spinal neurons may in part be due to the failure of a severed axon to take up RDA prior to the sealing of the cut end, i.e. must be freshly injured (Heimer and Zaborszky *Neuroanatomical tract-tracing methods 2: Recent Progress* (New York: Plenum, 1989)). Also the population of rubrospinal neurons that do not cross the brainstem will also appear as FG-positive cells in the "injured" nucleus Due to the small number of animals that were assessed, we did not attempt to quantify these results. Nevertheless, they probably represent an under-estimate of the axonal regeneration facilitated by immunological demyelination and myelin disruption, but definitely notan over-estimate of the degree of brainstem-spinal regeneration after myelin suppression.

As compared with prior art using spinal transection (Keirstead et al., (1995) *J. Neurosci.* 15:6963–6974, Keirstead et al., (1992) *Proc. Natl. Acad. Sci.* (USA) 89:11664–11668), the present invention is demonstrated using a hemisection model for this study so that each animal could serve as its own internal control (i.e. axonal regeneration from injured brainstem-spinal projections could be readily compared to the uninjured contralateral homologue). In addition, the present invention strove to minimize the degree of cyst cavity formation that often occurs with larger spinal lesions, as well as the amount of animal discomfort over the relatively long recovery periods required for this study.

Examinations for any functional or behavioral differences during the 5 week recovery period after experimental treatment indicated no notable differences in locomotor patterns between injured animals and uninjured control animals (i.e. all animals walked and all animals were comparable with respect to basic reflex functions). These observations were true regardless of the treatment infused intraspinally after a hemisection injury (e.g. PBS alone, GalC antibody alone, serum complement alone, or serum complement plus GalC antibody).

These findings indicate that the immunological suppression of myelin (demyelination and myelin disruption) facilitate anatomical regeneration of brainstem-spinal axons within the injured adult rat spinal cord.

EXAMPLE II

Effects of Removal of a Single Complement Protein on Immunological Demyelination Materials and Methods:

Surgical Spinal Transection and Transient Immunological Myelin Disruption:

Ten to 12 week old adult female rats (Sprague-Dawley), approximately 200 g in weight, were anaesthetized with Ketamine/Xylazine (60 mg/kg and 7.5 mg/kg, respectively) A limited dorsolateral laminectomy was performed at T10, and connected to an Alzet osmotic pump (14 day) to subsequently deliver a continuous intraspinal infusion (@ 0.5 µl/hr) of C3-depleted serum complement (Sigma S8788, 33% v/v) along with a complement-fixing IgG antibody to galactocerebroside (either our own polyclonal antibody or Chemicon Intl. Ltd., #AB 142,25% v/v) Cannulae were held in place by means of dental acrylic applied to the vertebral bone. Muscle layers were then sutured over the dental acrylic, and the superficial tissue and skin were closed.

All control animals were intraspinally infused via an osmotic pump, for the same time period, with whole human serum complement (SigmaS 1764,33% v/v) along with a complement-fixing IgG antibody to galactocerebroside (either our own polyclonal antibody or Chemicon Intl. Ltd., #AB142, 25% v/v). All surgical procedures and subsequent animal care protocols were in accordance with Canadian and University of British Columbia Animal Care Committee guidelines.

Electron microscopy was performed as described in Example 1.

Results:

As seen in FIGS. 5A–5C, the removal of the C3 component of complement results in a lack of myelin-removal. This indicates that this protein has a fundamental role in either (i) opsonization or (ii) the propagation of the cascade to the lytic membrane attack complex (MAC), the final lytic pathway complex.

EXAMPLE III

Regeneration of Chronically Injured Neurons

Materials and Methods: 11 animals (6 experimental and 5 control) were subjected to a left-side lateral hemisection of the T10 spinal cord as follows: 10 to 12 week old adult female rats (Sprague-Dawley), approximately 200 g in weight, were anaesthetized with Ketamine/Xylazine (60 mg/kg and 7.5 mg/kg, respectively) After a limited dorsolateral laminectomy at T10, a left-side spinal cord hemisection lesion was made with micro-scissors. The extent of the lesion was then confirmed by passing a sharp scalpel through the lesion site three times.

One month (5 animals) or 2 months (6 animals) after hemisection, an infusion cannula (connected to a 14 d osmotic pump) was inserted directly into the spinal cord 4–5 mm (1 spinal segment) caudal to the injury site. Cannulae were held in place by means of dental acrylic applied to the vertebral bone. Muscle layers were then sutured over the dental acrylic, and the superficial tissue and skin were closed. The osmotic pump delivered a continuous intraspinal infusion (0.5 µl/hr) of guinea-pig serum complement (33% v/v) along with a complement-fixing IgG antibody to galactocerebroside (either our own polyclonal antibody or Chemicon Intl. Ltd., #AB142, 0.25 mg/mL).

All control animals received an identical hemisection lesion and were then intraspinally infused via an osmotic pump for the same time period with whole guinea-pig serum complement (33% v/v) alone.

Animals were then allowed to recover for 28 days before Fluorogold was injected into the rostral lumbar, 1 cm (i.e. 3 spinal segments) caudal to the lesion site, as described in Example 1. After a further 7 days survival, each animal was killed, and the brain and spinal cord were removed for examination and analysis as described in Example 1.

The extent of the hemisection lesion was confirmed histologically at the end of both the 5-week treatment and the recovery period. All surgical procedures and subsequent animal care protocols were in accordance with Canadian and University of British Columbia Animal Care Committee guidelines.

Results:

The extent of the hemisection lesion was assessed in every animal. In all animals the region of the vestibulospinal tract was severed. The right side white matter tracts always remained intact and undamaged while the gray matter of the contralateral side usually remained undamaged.

Comparing "blind" counts of the number of labeled neurons within each LVe (FIG. 6), the data indicated that in the 1 month chronically injured animals, $31.5\%\pm5\%$ (n=3) of the injured lateral vestibulospinal neurons had regenerated a sufficient distance into the caudal lumbar cord to incorporate and retrogradely transport the Fluorogold. In contrast, control treated animals, receiving serum complement alone, did not exhibit a significant amount of LVe labeling: $3.6\%\pm2.7\%$, (n=2). Of those animals in which treatment was delayed for 2 months before treatment commenced, $26.8\%\pm13\%$ (n=3) of the injured lateral vestibulospinal neurons had regenerated a sufficient distance into the caudal lumbar cord to incorporate and retrogradely transport the Fluorogold. In contrast, control treated animals, receiving serum complement alone, did not exhibit a significant amount of LVe labeling: $5.4\%\pm1.8\%$, (n=2). These results indicate that the compositions of the present invention are useful for promoting regrowth, repair, and regeneration of chronically injured neurons in the CNS of a mammalian subject.

EXAMPLE IV

Surgical Spinal Transection and Transient Immunological Myelin Disruption

Ten to 12 week old adult female rats (Sprague-Dawley), approximately 200 g in weight, were anaesthetized with Ketamine/Xylazine (60 mg/kg, 7.5 mg/kg respectively). After a limited laminectomy at T10, a left-side spinal cord hemisection lesion was made with micro-scissors and the extent of the lesion was then confirmed by passing a sharp scalpel through the lesion site (FIGS. 7A–7E). Immediately after the lesion, an intraspinal cannula was implanted at T11 (n=22 total) and connected to an Alzet osmotic pump (14 day) to subsequently deliver a continuous intraspinal infusion (@ 0.5 µl/hr) of serum complement (GIBCO BRL, #19195-015, 33% v/v) along with a complement-fixing IgG antibody to galactocerebroside (either our own polyclonal antibody or Chemicon Intl. Ltd., #AB 142,25% v/v). Cannulae were held in place by means of dental acrylic applied to the vertebral bone. Muscle layers were then sutured over the dental acrylic, and the superficial tissue and skin closed. The extent of the hemisection lesion was always confirmed histologically at the end of the 5-week treatment and recovery period.

All control animals received an identical hemisection lesion and were then intraspinally infused via an osmotic pump for the same time period, with either vehicle alone (0.1 M phosphate buffered saline, PBS, n=5), antibody alone (25% v/v, n=2), or serum complement alone (33% v/v, n=6). All surgical procedures and subsequent animal care protocols were in accordance with Canadian and UBC Animal Care Committee guidelines.

Electron Microscopy:

Tissue for ultra structural analysis was obtained from 10–12 week old adult female Sprague-Dawley rats sacrificed 7 days after infusion of serum complement along with a complement-fixing IgG antibody to GalC (see above for details) via an osmotic pump. Animals were lethally anaesthetised with Ketamine/Xylazine (120 mg/kg, 15 mg/kg respectively), then perfused intracardially with 200 ml of 0.1M PBS (pH 7.4) followed by 100 ml of 4% glutaraldyhyde in 0.1M PB, (pH 7.3) and subsequently post fixed overnight in the same fixative. The infusion site and surrounding cord was cut into 1 mm transverse blocks and processed to preserve rostral-caudal sequence. Blocks were washed in 0.1M sodium cacodylate buffer (24 hours), post fixed in 2% OsO4, dehydrated through ascending alcohols and embedded in Spurrs' resin according to standard protocols. Tissue blocks from experimental and untreated-control animals were processed in parallel. Thins ections (1 $\mu$m) were cut from each block, stained with alkaline Toluidine Blue and examined under a light microscope. For electron microscopic examination blocks were trimmed and sections cut at 80–100 nm, mounted on copper grids, stained with uranyl acetate and lead citrate and viewed under a Ziess EM 10C electron microscope (at 80 kV).

Retrograde Neuronal Labeling:

Single Label Studies—

Twenty-eight days after the hemisection lesion and consequently 14 days after completion of the intraspinal infusion of the immunological reagents, each adult rat was anaesthetized with Ketamine/Xylazine (60 mg/kg, 7.5 mg/kg respectively). Fluorogold (FG, 100–150 nl total volume, 5% w/v in sterile dH$_2$O; Fluorochrome Inc. Englewood, Colo., USA) was injected (50–75 nl) bilaterally into the middle of the spinal tissue at the L1 level, approximately 1 cm caudal to the lesion site (FIGS. 7A–7E).

Double Label Studies—

At the time of lesion, the hemisection site was packed with gel-foam soaked with 12% (w/v in sterile dH$_2$O) rhodamine-conjugated dextran amine (RDA, 10,000 MW FluoroRuby, Molecular Probes) for 30 minutes. The gel-foam was then removed and the remaining surgical procedures were completed (as outlined above). After 28 days survival, all animals were anaesthetized with Ketamine/Xylazine (60 mg/kg, 7.5 mg/kg respectively) and FG (100–150 nl total volume, 5% w/vin sterile dH$_2$O) was injected (50–75 nl) bilaterally into the spinal parenchyma at the L1 level of the cord (n=6).

Analysis of Regeneration:

Seven days following the injection of the FG tracer into the lumbar cord, animals were lethally anaesthetised with Ketamine/Xylazine (120 mg/kg, 15 mg/kg respectively) and then perfused intracardially with 200 ml of 0.1M PBS (pH 7.4) followed by 100 ml of 4% paraformaldehyde in 0.1M PBS, (pH 7.3). The brain and spinal cord were then removed and postfixed overnight in the same fixative. Subsequently, each brain and spinal cord was cleared of fixative and cryo-preserved by placing the tissue in a series of sucrose solutions (15% followed by 21%). Coronal or parasagital sections were cut at 25 $\mu$m thickness on a cryostat. The brainstem and spinal cord tissue sections were examined under a Zeiss Axioskop with a 100 W mercury bulb (excitation/emission wavelength at: FG, 365/420 nm; RDA, 546/590 nm; fluorescein, 490/515 nm).

The two brainstem-spinal nuclei used to assess the axonal regenerative abilities of experimentally treated animals were the Red Nucleus (RN) (origin is contralateral to the hemisection) and the Lateral Vestibular (LVe) Nucleus (origin is ipsilateral to the hemisection). Spinal-projecting axons from each RN cross to the opposite side of the midbrain and descend throughout the spinal cord within the contralateral dorsolateral funiculus. This contralateral spinal projection pathway is known to be a completely lateralized tract with the possible exception of 2–5% of the axons which may project to the cord via an ipsilateral route (Waldron and Gwyn 1969, Brown, 1974; Huisman et al., 1981. Shieh et al., 1983). The LVe tract projects from the dorsolateral pontine hindbrain, maintaining an exclusive ipsilateral course throughout the brainstem and the ventrolateral white matter of the spinal cord (Zemlan et al., 1979, Shamboul, 1980).

Using a single-blind protocol, the number of retrograde labeled neurons within the Red Nucleus (RN) (contralateral to the hemisection) and the Lateral Vestibular (LVe) Nucleus (ipsilateral to the hemisection) were counted in every other tissue section (throughout these brainstem nuclei) to avoid counting the same neuron twice. Only those cells exhibiting a nucleus, a neuronal morphology (i.e. multi-polar in appearance) and specifically labeled with FG (i.e. not visible using other fluorescent filters, see above) extending into the proximal processes, were deemed to be positively labeled spinal-projecting neurons. The percentage of regenerating neurons for each brainstem-spinal projection was then determined in comparison to the number of labeled neurons within the contralateral (uninjured) control nucleus within the same animal.

Extent of Spinal Cord Demyelination and Myelin Disruption after Immunological Treatment Direct intraspinal infusion over 7 days (@ 0.5 $\mu$l/hr) of 33% heterologous (guinea pig) serum complement along with polyclonal antibodies to GalC (25%) in PBS resulted in extensive demyelination up to 2 mm away from the infusion cannula (total rostrocaudal distance of 4 mm or approximately 1 spinal segment (FIG. 2A). This zone of demyelination was bounded on either side by a further 8 mm or 2 segments of spinal cord characterized by disrupted myelin (i.e. myelin that is extensively de-laminated, having an unraveled appearance, FIG. 2B). As shown in previous studies (Keirstead et al., 1992,1995), control infusions of heterologous serum complement alone, myelin-specific antibody alone, or PBS alone resulted in only limited non-specific damage immediately centered around the cannula site. There was no surrounding zone of demyelination or myelin disruption (FIG. 2C).

The immunological demyelination and disruption of myelin within the experimentally-treated adult rat spinal cord was an active process extending throughout the entire cross-sectional profile of the cord. Immunological myelin disruption commenced within 1 day and was associated with an invasion of macrophages or resident microglia and polymorphonuclear cells (e.g. leukocytes such neutrophils, eosinophils and basophils). Many macrophages/microglia contained myelin fragments and completed their phagocytic activity within 7 days (FIG. 2D). This pattern of demyelination and myelin disruption could be maintained for as long as the serum complement and myelin-specific antibody were infused Recent evidence suggests that after the immunological infusion is terminated remyelination begins within 2 weeks (Keirstead and Blakemore, 1997, Dyer, Bourque and Steeves unpublished observations) and the new myelin originates from differentiating oligodendrocyte progenitors, although invading Schwann cells and surviving "mature" oligodendrocytes may also contribute to remyelination.

Choice of Retrograde Tracer and its Diffusion Distance from the Injection Site

In this study, the major anatomical evidence for axonal regeneration within the hemisected and immunologically myelin-suppressed spinal cord of adult rats depends on a comparison between the number of retrogradely-labeled neurons within a homologous pair of brainstem-spinal nuclei. For these comparisons to be valid, the candidate brainstem spinal nuclei must have highly unilateral projections that are confined to one side of the spinal cord at all levels. As summarized in FIG. 7A, a left thoracic hemisection severed the contralaterally-projecting magnocellular neurons of the right red nucleus (RN), but left the projections from the left RN undamaged (as they project through the intact right dorsolateral funiculus of the thoracic cord). Likewise, a left thoracic hemisection severed the ipsilateral projecting neurons of the left lateral vestibulospinal nucleus (LVe), but left the axons from the right LVe nucleus undamaged (as they also project through the intact right side of the thoracic cord via the ventrolateral white matter).

If a retrograde tracer (single label) is injected into the rostral lumbar cord (1 cm caudal to the injury site), it should be incorporated and transported back to the cell bodies of origin by both intact axons, as well as regenerated projections. Consequently, it is essential that the retrograde tracer reliably and extensively label most, if not all, descending spinal projection neurons. An equally important parameter is the tracer must be injected in a controlled and reproducible manner at a distance sufficiently caudal to the spinal injury to prevent any direct diffusion of the tracer to the level of the hemisection injury. The retrograde label that best satisfied all these conditions was Fluorogold (Sahibzada, et al., 1987). Fluorescent dextran amines, such as RDA, require a recent axonal injury to facilitate axonal uptake (c.f Heimer and Zaborszky, 1989), and were therefore better suited for use in the double label retrograde-tracing studies (see description below).

In all cases, the Fluorogold label (100–150 nl) was injected bilaterally within the rostral lumbar cord (1 cm or 2–3 spinal segments caudal to the hemisection injury site, FIGS. 7A–7E). We assessed the time course and degree of rostrocaudal diffusion of Fluorogold within the lumbar and thoracic spinal cord of normally myelinated (control) animals and experimentally treated rats (i.e. under demyelinated and myelin disrupted conditions). Random 25 $\mu$m sections of experimental and control-treated spinal cords (extending from L2 to T8) were examined under a fluorescent microscope using the highest intensity setting of the 100 W mercury lamp. Spinal tissue was examined for the extent of Fluorgold diffusion at varying survival intervals after injection, including: 12 hr (n=6), 24 hr (n=6), 3 d (n=6), 5 d (n=6) and 7 d (n=22). The maximum rostral diffusion distance observed was 4–6 mm (or 1–1.5 spinal segments) and occurred within a time span of 24 h. The degree of Fluorogold diffusion within the lumbar cord did not change over the subsequent time points examined (FIGS. 7A–7E).

Evidence for Braintem-spinal Axonal Regeneration by Retrograde Neuronal Labeling In brief, 28 animals, 12 experimental (9 retrogradely single-labeled, 3 double-labeled) and 16 control (13 retrogradely single-labeled, 3 double-labeled) were subjected to a left-side lateral hemisection of the T10 spinal cord. Immediately after hemisection, an infusion cannula (connected to a 14 d osmotic pump) was inserted directly into the spinal cord 4–5 mm (1 spinal segment) caudal to the injury site. The osmotic pump contained one of a number of 3 different control solutions or the experimental treatment (i.e. PBS vehicle alone, serum complement alone, anti-galactocerebroside antibody alone, or serum complement with anti-GalC antibodies, respectively). Animals were then allowed to recover for 28 days before the Fluorogold was injected into the rostral lumbar, 1 cm (i.e. at least 2 spinal segments) caudal to the lesion site. After a further 7 days survival, each animal was killed and the brain and spinal cord were removed for examination and analysis (see above for criteria used to determine a labeled neuron).

The extent of the hemisection lesion was assessed in every animal. In all but one experimental and one control-treated animal, the left thoracic spinal cord was hemisected (FIGS. 7A–7E). Most importantly, the regions of the rubrospinal tract (dorsolateral funiculus) and the lateral vestibulospinal tract (ventrolateral funiculus) were severed. The right side white matter tracts were always remained intact and undamaged and usually the gray matter of the uninjured side was also undamaged.

As discussed above, the 2 pairs of brainstem-spinal nuclei examined for evidence of retrograde labeling (after spinal cord hemisection and immunological myelin suppression) were the RN and the LVe. These brainstem-spinal nuclei were chosen for their unilateral projection patterns within the thoracic and lumbar cord, enabling comparisons to be made between the retrograde-labeling within an injured nucleus and the uninjured contralateral homologue. Comparing "blind" counts of the number of labeled neurons within each RN (FIGS. 3A–3B), the data indicated that 31.8%±4.7% (n=8, range 10–50%) of the injured magnocellular RN neurons had regenerated a sufficient distance into the caudal lumbar cord to incorporate and retrogradely transport the Fluorogold (FIG. 9). In contrast, control treated animals, receiving either the PBS vehicle alone, GalC antibody alone, or serum complement alone did not exhibit a significant amount of RN labeling, 1.49%±0.23%, (FIGS. 3C–3D. FIG. 9, n=13, range 0–3). The labeling of some neurons within the injured right RN nucleus may represent the small number of RN that do not project to the opposite side of the midbrain and descend within the ipsilateral (uninjured) cord (Shieh et al., 1983). No retrograde-labeling of cells was observed within the parvocellular region of the RN.

Retrograde-labeling of regenerating LVe neurons was also observed, but only after experimental demyelination and disruption of spinal cord myelin (FIGS. 8A–8E). In 8 experimental animals, the mean percentage of regenerating LVe labeling, in comparison to the uninjured contralateral control nucleus, was 41.8%±3.1% (n=8, range 33–49%). In control-treated animals (see above) the percent LVe labeling was 2.24%±0.55% (FIGS. 5A–5C, n=13, range 0–6).

Double retrograde labeling of the injured and myelin-suppressed rubrospinal tract was also qualitatively assessed (FIG. 9). Large numbers of RDA-positive (first label) magnocellular RN neurons were observed after direct labeling of the lesion site at the time of hemisection injury to the thoracic spinal cord. After intraspinal myelin-suppression and subsequent injection of Fluorogold caudal to the lesion site (see above for details) a small overlapping population of FG-positive neurons was observed (i.e. some neurons were labeled with both RDA and FG). Cells labeled exclusively by the first or the second tracer were also present in every brainstem analysed.

Examinations for any functional or behavioral differences during the 5 week recovery period after experimental treatment indicated no notable differences in locomotor patterns between injured animals and uninjured control animals (i.e.

all animals walked and all animals were comparable with respect to basic reflex functions). These occurred regardless of the treatment infused intraspinally after a hemisection injury (e.g. PBS alone, GalC antibody alone, serum complement alone, or serum complement plus GalC antibody). Thus, subtle differences were very difficult to observe or quantify and 'gross' motor patterns were essentially the same.

As compared with prior art using spinal transection (Keirstead et al., 1992, 1995), the present invention is demonstrated using a hemisection model so that each animal could serve as its own internal control (i.e. axonal regeneration from injured brainstem-spinal projections could be readily compared to the uninjured contralateral homologue). In addition, the present invention strove to minimize the degree of cyst cavity formation that often occurs with larger spinal lesions, as well as the amount of animal discomfort over the relatively long recovery periods required.

The present invention also illustrates that the demyelination produced by the intraspinal infusion of serum complement and a myelin-specific antibody (e.g. GalC) produced a rapid and active demyelination over 1–2 segments of the cord with myelin disruption extending a further 2 segments, either side of the infusion site. Resident microglia and/or invading macrophages were observed to contain myelin debris. The immunological suppression of spinal cord myelin surrounding the thoracic hemisection facilitated significant axonal regeneration by 2 unilaterally projecting brainstem-spinal pathways, the rubrospinal and lateral vestibulospinal (RN and LVe, respectively) tracts. Control treated animals (hemisection injury plus local intraspinal infusion of PBS alone. GalC antibody alone, or serum complement alone) showed little or no retrograde labeling within the injured RN or LVe.

TABLE 1

| Group | # cells labeled within axotomized Red nucleus | # cells labeled within uninjured Red nucleus | % axonal regeneration |
|---|---|---|---|
| experimental | 259 | 537 | 48.23 |
| | 168 | 426 | 39.44 |
| | 284 | 578 | 49.13 |
| | 35 | 349 | 10.03 |
| | 144 | 470 | 30.62 |
| | 65 | 314 | 20.7 |
| | 97 | 392 | 24.7 |
| | 106 | 313 | 33.9 |

TABLE 1-continued

| Group | # cells labeled within axotomized Red nucleus | # cells labeled within uninjured Red nucleus | % axonal regeneration |
|---|---|---|---|
| Mean ± s.d. | | | 31.8% ± 13.38% |
| control | 7 | 385 | 1.81 |
| | 11 | 385 | 2.86 |
| | 9 | 724 | 1.24 |
| | 17 | 671 | 2.5 |
| | 6 | 366 | 1.64 |
| | 5 | 809 | 0.62 |
| | 12 | 702 | 1.71 |
| | 1 | 166 | 0.6 |
| | 3 | 298 | 1.01 |
| | 5 | 371 | 1.35 |
| | 10 | 350 | 2.85 |
| | 23 | 556 | 4.14 |
| | 10 | 545 | 1.8 |
| Mean ± s.d. | | | 1.49% ± 0.84% |

What is claimed is:

1. A method for promoting neuron repair or regeneration in a human subject suffering from spinal cord disruption by intrathecal administration of a therapeutically effective amount of a composition comprising:
   (a) one or more complement-fixing antibodies or complement-fixing fragments thereof, which specifically bind to galactocerebroside (GalC); and
   (b) one or more complement proteins or fragments thereof, wherein at least one of the complement proteins is a C3 protein;
   wherein the combination of said antibodies and complement proteins or fragments thereof causes activation of the complement system resulting in disruption of myelin or demyelination, thereby promoting neuron repair or regeneration.

2. The method according to claim 1, wherein the complement-fixing antibodies fragments are selected from the group consisting of Fv, Fab, Fab', and F(ab')2 fragments.

3. The method according to claim 2, wherein the variable regions of the Fv fragment are linked by disulfide bonds or by a peptide linker.

4. The method according to claim 1, wherein the spinal cord disruption is caused by injury or trauma to the CNS.

5. The method according to claim 4, wherein the injury is a spinal cord injury.

* * * * *